(12) United States Patent
Kandimalla et al.

(10) Patent No.: US 9,096,858 B2
(45) Date of Patent: *Aug. 4, 2015

(54) IMMUNE REGULATORY OLIGONUCLEOTIDE (IRO) COMPOUNDS TO MODULATE TOLL-LIKE RECEPTOR BASED IMMUNE RESPONSE

(71) Applicant: Idera Pharmaceuticals, Inc., Cambridge, MA (US)

(72) Inventors: Ekambar R. Kandimalla, Cambridge, MA (US); Daqing Wang, Cambridge, MA (US); Ireneusz Nowak, Cambridge, MA (US); Sudhir Agrawal, Cambridge, MA (US)

(73) Assignee: Idera Pharmaceuticals, Inc., Cambridge, MA (US)

( * ) Notice: Subject to any disclaimer, the term of this patent is extended or adjusted under 35 U.S.C. 154(b) by 121 days.

This patent is subject to a terminal disclaimer.

(21) Appl. No.: 13/905,242

(22) Filed: May 30, 2013

(65) Prior Publication Data

US 2014/0004100 A1 Jan. 2, 2014

Related U.S. Application Data

(63) Continuation of application No. 13/299,555, filed on Nov. 18, 2011, now Pat. No. 8,486,908.

(60) Provisional application No. 61/415,494, filed on Nov. 19, 2010, provisional application No. 61/511,709, filed on Jul. 26, 2011.

(51) Int. Cl.
*C12N 15/117* (2010.01)
*A61K 31/7115* (2006.01)
*A61K 45/06* (2006.01)

(52) U.S. Cl.
CPC .......... *C12N 15/117* (2013.01); *A61K 31/7115* (2013.01); *A61K 45/06* (2013.01); *C12N 2310/17* (2013.01); *C12N 2310/317* (2013.01); *C12N 2310/51* (2013.01); *C12N 2310/52* (2013.01)

(58) Field of Classification Search
USPC .......... 435/6.1, 91.1, 375, 455, 458; 514/1, 2, 514/44; 536/23.1
See application file for complete search history.

(56) References Cited

U.S. PATENT DOCUMENTS

| | | |
|---|---|---|
| 6,426,334 B1 | 7/2002 | Agrawal et al. |
| 6,476,000 B1 | 11/2002 | Agrawal |
| 6,815,429 B2 | 11/2004 | Agrawal |
| 7,105,495 B2 | 9/2006 | Agrawal et al. |
| 7,115,579 B2 | 10/2006 | Agrawal et al. |
| 7,517,862 B2 | 4/2009 | Agrawal et al. ............ 514/44 R |
| 8,486,908 B2 * | 7/2013 | Kandimalla et al. ........ 514/44 R |
| 2003/0059482 A1 | 3/2003 | Siskind |
| 2004/0009949 A1 | 1/2004 | Krieg |
| 2004/0097719 A1 | 5/2004 | Agrawal et al. |
| 2005/0059616 A1 | 3/2005 | Kelly et al. |
| 2005/0239733 A1 | 10/2005 | Jurk et al. |
| 2006/0193869 A1 | 8/2006 | Barrat et al. |
| 2007/0238678 A1 | 10/2007 | Barrat et al. |
| 2008/0089883 A1 | 4/2008 | Kandimalla et al. |
| 2009/0053148 A1 | 2/2009 | Kandimalla et al. |
| 2009/0060898 A1 | 3/2009 | Kandimalla et al. |
| 2009/0081198 A1 | 3/2009 | Kandimalla et al. |
| 2009/0087388 A1 | 4/2009 | Kandimalla et al. |
| 2009/0098063 A1 | 4/2009 | Kandimalla et al. |
| 2009/0131512 A1 | 5/2009 | Barrat et al. |
| 2010/0098685 A1 | 4/2010 | Zhu et al. |
| 2011/0003885 A1 | 1/2011 | Barrat et al. |
| 2011/0009477 A1 | 1/2011 | Yu et al. |
| 2011/0171209 A1 | 7/2011 | Zhu et al. |

FOREIGN PATENT DOCUMENTS

| | | |
|---|---|---|
| WO | 03/103586 A2 | 12/2003 |
| WO | WO 2005/058349 | 6/2005 |
| WO | WO 2006/063072 | 6/2006 |
| WO | 2009/154609 A1 | 12/2009 |

OTHER PUBLICATIONS

Petar Lenert, Inhibitory Oligonucleotides Block the Induction of AP-1 Transcription Factor by Stimulatory CpG Oligonucleotides in B Cells; Antisense and Nucleic Acid Drug Development 13:143-150 (2003).

Hornung et al., "Quantitative expression of toll-like receptor 1-10 mRNA in cellular subsets offhuman peripheral blood mononuclear cells and sensitivity to CpGh oligodeoxymicieotides", Journal of Immunology, 2002, 168, pp. 4531-4537.

Poltorak et al., "Defective LPS signaling in C3H/HeJ and C57BL/10ScCr mice: mutations in Tlr4 gene", Science, vol. 282, Dec. 11, 1998, pp. 2085-2088.

Underhill et al., "The toll-like receptor 2 is recruited to macrophage phagosomes and discriminates between pathogens", Nature, vol. 401, Oct. 21, 1999, pp. 811-815.

Hayashi et al., "The innate immune response to bacterial flagellin is mediated by toll-like receptor 5", Nature, vol. 410, Apr. 26, 2001, pp. 1099-1103.

(Continued)

*Primary Examiner* — Jane Zara
(74) *Attorney, Agent, or Firm* — Elmore Patent Law Group, P.C.; Joseph C. Zucchero; Carolyn S. Elmore, Esq.

(57) ABSTRACT

The invention provides novel immune regulatory oligonucleotides (IRO) as antagonist of TLRs and methods of use thereof. These IROs have unique sequences that inhibit or suppress TLR-mediated signaling in response to a TLR ligand or TLR agonist. The methods may have use in the prevention and treatment of cancer, an autoimmune disorder, airway inflammation, inflammatory disorders, infectious disease, skin disorders, allergy, asthma or a disease caused by a pathogen.

8 Claims, 12 Drawing Sheets

(56) References Cited

OTHER PUBLICATIONS

Zhang et al., "A toll-like receptor that prevents infection by uropathogenic bacteria" Science 303, 1522, 2004, pp. 1522-1526.
Meier et al., "Toll-like receptor (TLR) 2 and TLR4 are essential for aspergillus-induced activation of murine macrophages", Cellular Microbiology, 2003, 5(8), pp. 561-570.
Campos et al., "Activation of toll-like receptor-2 by glycosylphosphatidylinositol anchors from a protozoan parasite", Journal of Immunology, 167, 2001, pp. 416-423.
Hoebe et al., "Identification of Lps2 as a key transducer of MyD88-independent TIR signaling", Nature, vol. 424, Aug. 14, 2003, pp. 743-748.
Lund et al., "Toll-like receptor 9-mediated recognition of herpes simplex virus-2 by plasmacytoid dendritic cells", The Journal of Experimental Medicine, 198, 2003, pp. 513-520.
Heil et al., "Species-specific recognition of single-stranded RNA via toll-like receptor 7 and 8", Science, 303, 1526, 2004, pp. 1526-1529.
Diebold et al., "Innate antiviral responses by means of TLR7-mediated recognition of single-stranded RNA", Science, 303, 1529, 2004, pp. 1529-1531.
Hornung et al., "Replication-dependent potent IFN-α induction in human plasmacytoid dendritic cells by a single-stranded RNA virus", The Journal of Immunology, 173, 2004, pp. 5935-5943.
Akira et al., "Toll-like receptors: critical proteins linking innate and acquired immunity", Nature Immunology, 2, 2001, pp. 675-680.
Medzhitov, "Toll-like receptors and innate immunity", Nature Reviews Immunology, vol. 1, Nov. 2001, pp. 135-145.
Cook et al., "Toll-like receptors in the pathogenesis of human disease", Nature Immunology, vol. 5, No. 10, Oct. 2004, pp. 975-979.
Liew et al., "Negative regulation of toll-like receptor-mediated immune responses", Nature, vol. 5, Jun. 2005, pp. 446-458.
Hemmi et al., "Small anti-viral compounds activate immune cells via the TLR7 MyD88-dependent signaling pathway", National Immunology, Jan. 22, 2002, pp. 196-200.
Jurk et al., "Human TLR7 or TLR8 independently confer responsiveness to the antiviral compound R-848", National Immunology, Jun. 2002, pp. 499.
Lee et al., "Molecular basis for the immunostimulatory activity of guanine nucleoside analogs: activation of toll-like receptor 7", Proceedings of the National Academy of Sciences USA, May 27, 2003, vol. 100, No. 11, pp. 6646-6651.
Alexopoulou et al., "Recognition of double-stranded RNA and activation of NF-kB by toll-like receptor 3", Nature, vol. 413, Oct. 18, 2001, pp. 732-738.
Tokunaga et al., "Antitumor Activity of Deoxyribonucleic Acid Fraction from Mycobacterium bovis BCG. I. Isolation. Physicochemical Characterization, and Antitumor Activity", J. Natl. Cancer Inst. 1984 72 : pp. 955-962.
Shimada et al. "In vivo augmentation of natural killer cell activity with a deoxyribonucleic acid fraction of BCG", Japanese Journal of Cancer Research, 77, Aug. 1986, pp. 808-816.
Yamamoto et al., "In vitro augmentation of natural killer cell activity and production of interferon α/β and ⊤ with deoxyribonucleic acid fraction from mycobaderium bovis BCG", Japanese Journal of Cancer Research, 70, Jul. 1988, pp. 866-873.
Zhao et al., "Effect of Different Chemically Modified Oligodeoxynucleotides on Immune Stimulation," Biocehm. Pharmacol., 1996, 51 pp. 173-182.
Hemmi H., et al., "A Toll-Like Receptor Recognizes Bacterial DNA", Nature 408; 2000, pp. 740-745.
Zhao et al., "Modulation of Oligonucleotide-Induced Immune Stimulation by Cyclodextrin Analogs," Biochem. Pharmacol., 1996 52: pp. 1537-1544.
Zhao et al., "Pattern and kinetics of cytokine production following administration of phosphorothioate oligonucleotides in mice", Antisense and Nucleic Acid Drug Development, 1997, 7, pp. 495-502.

Zhao et al., "Site of Chemical Modifications in CpG Containing Phosphorothioate Oligonucleotide Modulates its Immunostimulatory Activity," Bioorg. Med. Chem. Lett., 1999, 9, pp. 3453-3458.
Zhao et al., "Immunostimulatory Activity of CpG Containing Phosphorothioate Oligodeoxynucleotide is modulated by modification of a Singe Deoxynucleoside," Bioorg. Med.Chem. Lett., 2000, 10 pp. 1051-1054.
Yu et al., "Accessible 5'-End of CpG containing Phosphorothioate Oligodeoxynucleotides is essential for immunostimulatory activity," Bioorg. Med. Chem. Lett., 2000 10 pp. 2585-2588.
Yu et al., "Modulation of Immunostimulatory Activity of CpG Oligonucleotidesby site-specific deletion of nucleobases," Bioorg. Med. Chem. Lett., 2001, 11 pp. 2263-2267.
Kandimalla et al., "Effect of Chemical Modifications of Cytosine and Guanine in a CpG motif of oligonucleotides: Structure-Immunostimulatory Activity relationships," Bioorg. Med. Chem., 2001, 9 pp. 807-813.
Kandimalla et al., "Immunomodulatory oligonucleotides containing a cytosine-phosphate-2'-deoxy-7-deazaguanosine motif as potent Toll-like receptor 9 agonists," PNAS 102(19), 2005 pp. 6925-6930.
Kandimalla et al., "A dinucleotide motif in oligonucleotides shows potent immunomodulatory activity and overrides species-specific recognition observed with CpG motif", PNAS, 100, pp. 14303-14308.
Cong et al., "Self-stabilized CpG DNAs optimally activate human B cells and plasmacytoid dendritic cells", Biochemical and Biophysical Research Communications; 2003, 310(4): 1133-1139.
Kandimalla et al, "Secondary Structures in CpG Oligonucleotides affect Immunostimulatory Activity", Biochem. Biophys. Res. Commun., 2003, 306: 948-953.
Kandimalla et al., "Divergent synthetic nucleotide motif recognition pattern: design and development of potent immunomodulatory oligodeoxyribonucleotide agents with distinct cytokine induction profiles", Nucleic Acid Research vol. 31, No. 9, 2003, pp. 2393-2400.
Yu et al., "Requirement of Nucleobase Proximal to CpG Dinucleotide for Immunostimulatory Activity of Synthetic CpD DNA," Bioorg. & Med. Chem., 2003, 11(3):459-464.
Bhagat et al., "CpG Penta- and Hexadeoxyribonucleotides as Potent Immunomodulatory Agents," Biochem. Biophys. Res. Comm., 2003, 300(4):853-861.
Yu et al., "Immunomers'-Novel 3'-3'-Linked CpG Oligodeoxyribonucleotides as Potent Immunomodulatory Agents," Nucleic Acid Res., 2002, 30(20):4460-4469.
Yu et al., "Design, synthesis, and immunostimulatory properties of CpG DNAs containing alkyl-linker substitutions: role of nucleosides in the flanking sequences", J. Med. Chem, 2002, 45, pp. 4540-4548.
Yu D., et al., "Potent CpG Oligonucleotides Containing Phosphodiester Linkages: in vitro and in vivo immunostimulatory properties", Biochem. Biophys. Res. Commun. 297: 83-90 (2002).
Kandimalla et al., "Conjugation of ligands at the 5'-end of CpG DNA affects immunostimulatory activity", Bioconjugate Chem. 13:966-974 (2002).
Yu et al., "Immunostimulatory activity of CpG oligonucleotides containing non-ionic methylphosphonate linkages", Bioorganic & Medicinal Chemistry 9, 2001, pp. 2803-2808.
Putta et al., "Novel oligodeoxynueleotide agonists of TLR9 containing $N^3$-Me-dC or $N^{J}$-Me-dG modifications", Nucleic Acids Research, 2006, vol. 34, No. 11, pp. 3231-3238.
Lenert et al., "Structural characterization of the inhibitory DNA motif for the type A (D)-CpG-induced cytokine secretion and NK-cell lytic activity in mouse spleen cells", DNA and Cell Biology, vol, 22, No. 10, 2003, pp. 621-631.
Chen et al., "Identification of methylated CpG motifs as inhibitors of the immune stimulatory CpG motifs", Gene Therapy, 2001, 8, pp. 1024-1032.
Stunz et al, "Inhibitory oligonucleotides specifically block effects of stimulatory CpG oligonucleotides in B cells", Eur. J. Immunol. 2002, 32, pp. 1212-1222.
Duramad et al., "Inhibitors of TLR-9 act on multiple cell subsets in mouse and man in vitro and prevent death in vivo from systemic inflammation", The Journal of Immunology, 2005, 174, pp. 5193-5200.

(56) References Cited

OTHER PUBLICATIONS

Patole et al., "G-rich DNA suppresses systemic lupus", J. Am. Soc. Nephrol, 16, 2005, pp. 3273-3280.
Gursel et al., "Repetitive elements in mammalian telomeres suppress bacterial DNA-induced immune activation", The Journal of Immunology, 2003, 171, pp. 1393-1400.
Shirota et al., "Suppressive oligodeoxynucleotides inhibit Th1 differentiation by blocking IFN-y- and IL-12-mediated signaling", The Journal of Immunology, 2004, 173, pp. 5002-5007.
Verthelyi et al., "Human peripheral blood cells differentially recognize and respond to two distinct CpG motifs", The Journal of Immunology, 2001, 166, pp. 2372-2377.
Gursel et al., "Differential and competitive activation of human immune cells by distinct classes of CpG oligodeoxynuceleotide", Journal of Leukocyte Biology, May 2002, vol. 71, pp. 813-820.
Krug et al., "Identification of CpG oligonucleotide sequences with high induction of IFN-α/β in plasmacytoid dendritic cells", Eur. J. Immunol, 2001, 31, pp. 2154-2163.
Banns et al., "Divergent therapeutic and immunologic effects of oligodeoxynucleotides with distinct CpG motifs", The Journal of Immunology, 2001, 167, pp. 4878-4886.
Verthelyi et al., "CpG oligodeoxynucleotides protect normal and SIV-infected macaques from Leishmania infection", The Journal of Immunology, 2003, 170, pp. 4717-4723.
McShan et al., "Inhibition of transcription of HIV-a in infected human cells by oligodeoxynucleotides designed to form DNA triple helices", The Journal of Biological Chemistry, Mar. 15, 1992, vol. 267, No. 8, pp. 5712-5721.
Rando et al., "Suppression of human immunodeficiency virus type I activity in vitro by oligonucleotides which form intramolecular tetrads", The Journal of Biological Chemistry, Jan. 27, 1995, vol. 270, No. 4, pp. 1754-1760.
Benimetskaya et al., "Formation of a G-tetrad and higher order structures correlates with biological activity of the RelA (NF-KB p65) 'antisense' oligodeoxynucleotide", Nucleic Acids Research, 1997, vol. 25, No. 13, pp. 2648-2656.
Bock et al., "Selection of single-stranded DNA molecules that bind and inhibit human thrombin" Nature, Feb. 6, 1992, vol. 355, pp. 564-566.
Uhlmann et al., "Antisense Oligonucleotides: A new Therapeutic Principle," Chemical Revies, 1990, 90(4), pp. 543-584.
Hunziker et al., "Nucleic acid analogues: synthesis and properties", Mod. Syn. Methods, 1995, 7, pp. 331-417.
Crook et al., "Progress in antisense oligonucleotide therapeutics", Annu. Rev. Pharmacol. Toxicol., 1996, 36, pp. 107-129.
Noronha et al., "Synthesis and biophysical properties of arabinonucleic acids (ANA): circular dichroic spectra, melting temperatures, and ribonuclease H susceptibility of ANA RNA hybrid duplexes", Biochemistry, 2000, 39, pp. 7050-7062.
Yu, D., et al., "Modifications Incorporated in CpG Motifs of Oligodeoxynucleotides Lead to Antagonist Activity of Toll-like Receptors 7 and 9," J. Med. Chem., 52(16), 5108-5114 (2009).

* cited by examiner

Figure 1. Linear synthesis of immune regulatory oligonucleotides.

A

B

IMMUNE REGULATORY OLIGONUCLEOTIDE (IRO) COMPOUNDS TO MODULATE TOLL-LIKE RECEPTOR BASED IMMUNE RESPONSE

BACKGROUND OF THE INVENTION

Field of the Invention

The invention generally relates to the field of immunology and immunotherapy, and more specifically to immune regulatory oligonucleotide (IRO) compositions and their use for inhibition and/or suppression of Toll-like Receptor-mediated immune responses. In particular, the invention relates to antagonists of Toll-Like Receptors 7 (TLR7) and/or TLR9 that uniquely inhibit cytokines normally produced through TLR7 and/or TLR9 stimulation.

SUMMARY OF THE RELATED ART

Toll-like receptors (TLRs) are present on many cells of the immune system and have been shown to be involved in the innate immune response (Hornung, V. et al., (2002) J. Immunol. 168:4531-4537). In vertebrates, or mammals, this family consists of ten proteins called TLR1 to TLR10, which are known to recognize pathogen associated molecular patterns from bacteria, fungi, parasites, and viruses (Poltorak, a. et al. (1998) Science 282:2085-2088; Underhill, D. M., et al. (1999) Nature 401:811-815; Hayashi, F. et. al (2001) Nature 410:1099-1103; Zhang, D. et al. (2004) Science 303:1522-1526; Meier, A. et al. (2003) Cell. Microbiol. 5:561-570; Campos, M. A. et al. (2001) J. Immunol. 167: 416-423; Hoebe, K. et al. (2003) Nature 424: 743-748; Lund, J. (2003) J. Exp. Med. 198:513-520; Heil, F. et al. (2004) Science 303:1526-1529; Diebold, S. S., et al. (2004) Science 303: 1529-1531; Hornung, V. et al. (2004) J. Immunol. 173:5935-5943). TLRs are a key means by which mammals recognize and mount an immune response to foreign molecules and also provide a means by which the innate and adaptive immune responses are linked (Akira, S. et al. (2001) Nature Immunol. 2:675-680; Medzhitov, R. (2001) Nature Rev. Immunol. 1:135-145). TLRs have also been shown to play a role in the pathogenesis of many diseases, including autoimmunity, infectious disease, and inflammation (Cook, D. N. et al. (2004) Nature Immunol. 5:975-979) and the regulation of TLR-mediated activation using appropriate agents may provide a means for disease intervention.

Some TLRs are located on the cell surface to detect and initiate a response to extracellular pathogens and other TLRs are located inside the cell to detect and initiate a response to intracellular pathogens. Table 1 provides a representation of TLRs, their cellular location, and the known agonists therefore (Diebold, S. S. et al. (2004) Science 303:1529-1531; Liew, F. et al. (2005) Nature 5:446-458; Hemmi H et al. (2002) Nat Immunol 3:196-200; Jurk M et al., (2002) Nat Immunol 3:499; Lee J et al. (2003) Proc. Natl. Acad. Sci. USA 100:6646-6651); (Alexopoulou, L. (2001) Nature 413: 732-738).

TABLE 1

| TLR Molecule | Agonist |
| --- | --- |
| Cell Surface TLRs: | |
| TLR2 | bacterial lipopeptides |
| TLR4 | gram negative bacteria |
| TLR5 | motile bacteria |
| TLR6 | gram positive bacteria |
| Endosomal TLRs: | |
| TLR3 | double stranded RNA viruses |
| TLR7 | single stranded RNA viruses |
| TLR8 | single stranded RNA viruses |
| TLR9 | unmethylated DNA |

Certain unmethylated CpG motifs present in bacterial and synthetic DNA have been shown to activate the immune system and induce antitumor activity. (Tokunaga T et al., J. Natl. Cancer Inst. (1984) 72:955-962; Shimada S, et al., Jpn. H cancer Res, 1986, 77, 808-816; Yamamoto S, et al., Jpn. J. Cancer Res., 1986, 79, 866-73). Other studies using antisense oligonucleotides containing CpG dinucleotides have been shown to stimulate immune responses (Zhao Q, et al. (1996) Biochem. Pharmacol. 26:173-182). Subsequent studies demonstrated that TLR9 recognizes unmethylated CpG motifs present in bacterial and synthetic DNA (Hemmi, H. et al. (2000) Nature 408:740-745). Other modifications of CpG-containing phosphorothioate oligonucleotides can also affect their ability to act as modulators of immune response through TLR9 (see, e.g., Zhao et al., Biochem. Pharmacol. (1996) 51:173-182; Zhao et al. (1996) Biochem Pharmacol. 52:1537-1544; Zhao et al. (1997) Antisense Nucleic Acid Drug Dev. 7:495-502; Zhao et al (1999) Bioorg. Med. Chem. Lett. 9:3453-3458; Zhao et al. (2000) Bioorg. Med. Chem. Lett. 10:1051-1054; Yu, D. et al. (2000) Bioorg. Med. Chem. Lett. 10:2585-2588; Yu, D. et al. (2001) Bioorg. Med. Chem. Lett. 11:2263-2267; and Kandimalla, E. et al. (2001) Bioorg. Med. Chem. 9:807-813). In addition, structure activity relationship studies have allowed identification of synthetic motifs and novel DNA-based compounds that induce specific immune response profiles that are distinct from those resulting from unmethylated CpG dinucleotides. (Kandimalla, E. et al. (2005) Proc. Natl. Acad. Sci. USA 102:6925-6930. Kandimalla, E. et al. (2003) Proc. Nat. Acad. Sci. USA 100: 14303-14308; Cong, Y. et al. (2003) Biochem Biophys Res. Commun.310:1133-1139; Kandimalla, E. et al. (2003) Biochem. Biophys. Res. Commun. 306:948-953; Kandimalla, E. et al. (2003) Nucleic Acids Res. 31:2393-2400; Yu, D. et al. (2003) Bioorg. Med. Chem.11:459-464; Bhagat, L. et al. (2003) Biochem. Biophys. Res. Commun.300:853-861; Yu, D. et al. (2002) Nucleic Acids Res.30:4460-4469; Yu, D. et al. (2002) J. Med. Chem.45:4540-4548. Yu, D. et al. (2002) Biochem. Biophys. Res. Commun.297:83-90; Kandimalla. E. et al. (2002) Bioconjug. Chem.13:966-974; Yu, D. et al. (2002) Nucleic Acids Res. 30:1613-1619; Yu, D. et al. (2001) Bioorg. Med. Chem. 9:2803-2808; Yu, D. et al. (2001) Bioorg. Med. Chem. Lett. 11:2263-2267; Kandimalla, E. et al. (2001) Bioorg. Med. Chem. 9:807-813; Yu, D. et al. (2000) Bioorg. Med. Chem. Lett. 10:2585-2588; Putta, M. et al. (2006) Nucleic Acids Res. 34:3231-3238).

The selective localization of TLRs and the signaling generated therefrom, provides some insight into their role in the immune response. The immune response involves both an innate and an adaptive response based upon the subset of cells involved in the response. For example, the T helper (Th) cells involved in classical cell-mediated functions such as delayed-type hypersensitivity and activation of cytotoxic T lymphocytes (CTLs) are Th1 cells. This response is the body's innate response to antigen (e.g. viral infections, intracellular pathogens, and tumor cells), and results in a secretion of IFNgamma and a concomitant activation of CTLs. Alternatively, the Th cells involved as helper cells for B-cell activation are Th2 cells. Th2 cells have been shown to be activated in response to bacteria and parasites and may mediate the body's adaptive immune response (e.g. IgE production and eosinophil activation) through the secretion of IL-4 and IL-5. The type of immune response is influenced by the cytokines produced in response to antigen exposure and the differences in the cytokines secreted by Th1 and Th2 cells may be the result of the different biological functions of these two subsets.

While activation of TLRs is involved in mounting an immune response, an uncontrolled stimulation of the immune system through TLRs may exacerbate certain diseases in immune compromised subjects. In recent years, several groups have shown the use of synthetic oligodeoxyoligonucleotides (ODNs) as inhibitors of inflammatory cytokines (Lenert, P. et al. (2003) DNA Cell Biol. 22(10):621-631).

Using certain synthetic ODNs, Lenert et al. report the ability to produce inhibitory ODNs (Lenert, P. et al. (2003) DNA Cell Biol. 22(10):621-631). These inhibitory ODN require two triplet sequences, a proximal "CCT" triplet and a distal "GGG" triplet. In addition to these triplet-containing inhibitory ODNs, several groups have reported other specific DNA sequences that could inhibit TLR-9-mediated activation by CpG-containing ODNs. These "inhibitory" or "suppressive" motifs are rich in poly "G" (e.g. "GGGG") or "GC" sequences, tend to be methylated, and are present in the DNA of mammals and certain viruses (see e.g.,; Chen, Y., et al., Gene Ther. 8: 1024-1032 (2001); Stunz, L. L., Eur. J. Immunol. 32: 1212-1222 (2002). Duramad, O., et al., J. Immunol., 174: 5193-5200 (2005) and Jurk et. al (US 2005/0239733), describe a structure for inhibitory DNA oligonucleotides containing a GGGG motif within the sequences. Patole et al. demonstrate that GGGG containing ODNs will suppress systemic lupus (Patole, P. et al. (2005) J. Am. Soc. Nephrol. 16:3273-3280). Additionally, Gursel, I., et al., J. Immunol., 171: 1393-1400 (2003), describe repetitive TTAGGG elements, which are present at high frequency in mammalian telomeres, down-regulate CpG-induced immune activation. Shirota, H., et al., J. Immunol., 173: 5002-5007 (2004), demonstrate that synthetic oligonucleotides containing the TTAGGG element mimic this activity and could be effective in the prevention/treatment of certain Th1-dependent autoimmune diseases.

In contrast, some studies have called into question the view that poly G containing ODNs are acting as antagonists of TLRs. For example, U.S. Pat. No. 6,426,334, Agrawal et al., demonstrate that administering CpG oligonucleotides containing GGGG strings have potent antiviral and anticancer activity and that administration of these compounds will cause an increase in serum IL-12 concentration. Further, CpG oligos containing polyG sequences are known to induce immune responses through TLR9 activation (Verthelyi D et al, J Immunol. 166, 2372, 2001; Gursel M et al, J Leukoc Biol, 71, 813, 2001, Krug A et al, Eur J Immunol, 31, 2154, 2001) and show antitumor and antiviral activities (Ballas G K et al, J Immunol, 167, 4878, 2001; Verthelyi D et al, J Immunol, 170, 4717, 2003). In addition, polyG oligonucleotides are known to inhibit HIV and Rel A (McShan W M, et al, J Biol Chem., 267(8):5712-21, 1992; Rando, R F et al., J Biol Chem, 270(4):1754-60, 1995; Benimetskaya L, et al., Nucleic Acids Res., 25(13):2648-56, 1997); and ODNs containing an immune stimulatory CpG motif and 4 consecutive G nucleotides (known as class A ODNs) induce interferon-y production and a Th1 shift in the immune response. Moreover, in preclinical disease models, Class A ODNs have been shown to induce a TLR-mediated immune response.

As an additional limitation, oligonucleotides containing guanosine strings have been shown to form tetraplex structures, act as aptamers, and inhibit thrombin activity (Bock L C et al., Nature, 355:564-6, 1992; Padmanabhan, K et al., J Biol Chem., 268(24):17651-4, 1993). Thus, it is not clear whether single-stranded or multiple-stranded structures are effective at suppressing TLR9 activation.

Kandimalla et al. (11/549,048) describe a novel class of TLR antagonists that do not require a polyG sequence. Kandimalla et al. also describes the application of these novel compositions to treating and preventing various diseases and disorders (11/549,048; 11/743,876; 12/140,334; 12/140,338; 12/244199). However a challenge remains to develop additional TLR antagonists that do not require a polyG sequence and thus do not present the problem of forming secondary structures. This challenge may be solved through the design of new oligonucleotide-based compounds and compositions that can act as unique inhibitors of TLRs 7 and/or 9. Such new custom compounds and compositions will find use in many clinically relevant applications, including treating and preventing diseases and disorders with an immune stimulatory component.

BRIEF SUMMARY OF THE INVENTION

The inventors have surprisingly discovered that uniquely modifying the nucleic acid sequence on the 5'-side of a core immune stimulatory dinucleotide, the nucleic acids within the core immune stimulatory dinucleotide, the linkages between nucleotides or the linkers connecting two or more oligonucleotides produces novel antagonists of TLR7 and/or TLR9 that distinctly antagonize, inhibit, suppress or prevent the in vitro and in vivo cytokine and chemokine profiles normally generated through TLR7 and/or TLR9 stimulation. This ability to antagonize, inhibit suppress or prevent the cytokine and chemokine response to a TLR7 and/or TLR9 agonist provides the ability to prevent and/or treat various disease conditions in a disease-specific and even a patient-specific manner.

Thus, the invention provides immune regulatory oligonucleotides (IRO) compounds that act as distinct antagonists of TLR7 and/or TLR9 and methods of using such compounds to antagonize, inhibit, suppress or prevent TLR7- and/or TLR9-mediated immune stimulation. These IRO compounds comprise an immune stimulatory motif and would be immune stimulatory but for one or more chemical modifications in the nucleic acid sequence on the 5'-side of the immune stimulatory motif and/or in the immune stimulatory motif. The IRO compounds and compositions that preferentially antagonize, inhibit, suppress or prevent the activity of TLR7 and/or TLR9 have the structure 5'-$N_m$—$N_3N_2N_1$CG$N^1N^2N^3$—$N^m$-3' (SEQ ID NO: 70), wherein CG is an oligonucleotide motif selected from CpG, C*pG, C*pG* or CpG* wherein C is cytosine, C* is a cytosine analog or derivative, G is a guanine and G* is a guanine analog or derivative; $N_1$—$N_3$, at each occurrence, is independently a nucleotide or nucleotide derivative; $N^1$—$N^3$, at each occurrence, is independently a nucleotide or nucleotide derivative; $N_m$ and $N^m$, at each occurrence, is independently a nucleotide, nucleotide derivative or non-nucleotide linker; provided that at least one of $N_1$, $N_2$, and $N_3$ and/or C and/or G of the oligonucleotide motif is a nucleotide derivative that antagonizes, inhibits, suppresses or prevents the activity of the oligonucleotide motif; and further provided that the compound contains less than 4 consecutive guanosine nucleotides and preferably less than 3 consecutive guanosines, wherein the immune stimulatory activity of the oligonucleotide motif is antagonized, inhibited, suppressed or prevented by the nucleotide derivative; and wherein m is a number from 0 to about 30.

In some embodiments, the IRO compounds may comprise at least two oligonucleotides, wherein at least two oligonucleotides are covalently linked via a direct nucleotide to nucleotide linkage at their 3' ends through the 3' positions of the sugars or through a modified sugar or modified nucleobase or via a non-nucleotide linker at their 3' ends through the 3' positions of the sugars or through a modified sugar or modified nucleobase. In preferred aspects of this embodiment, at least one of oligonucleotides of the IRO compound has the structure 5'-$N_m$—$N_3N_2N_1$CG$N^1N^2N^3$—$N^m$-3' (SEQ ID NO: 70), wherein $N_m$, $N_1$, $N_2$, $N_3$, C, G, $N^1$, $N^2$, $N^3$ and $N^m$ are as described above for the general structure of the IRO compound. In more preferred aspects of this embodiment, at least two of the oligonucleotides of the IRO compound have the structure 5'-$N_m$—$N_3N_2N_1$CG$N^1N^2N^3$—$N^m$-3' (SEQ ID NO: 70), wherein $N_m$, $N_1$, $N_2$, $N_3$, C, G, $N^1$, $N^2$, $N^3$ and $N^m$ are as described above for the general structure of the IRO compound. Such an IRO compound may have the structure 5'-$N_m$—$N_3N_2N_1$CG$N^1N^2N^3$—$N^m$-3' - X -3'-$N^m$—$N^3N^2N^1$GC$N_1N_2N_3$—$N_m$-5' (5'- SEQ ID NO: 70-3'- X -3'- SEQ ID NO: 70-5'), wherein X is a nucleotide linkage or a non-nucleotide linker and $N_m$, $N_1$, $N_2$, $N_3$, C, G, $N^1$, $N^2$, $N^3$ and $N^m$ are as described above for the general structure of the IRO compound.

The IRO compounds and compositions according to the invention preferentially inhibit TLR7 and/or TLR9-mediated immune responses in various cell types and in various in vitro and in vivo experimental models, with each compound or composition providing a distinct immune inhibition profile.

The invention further provides for a pharmaceutical composition comprising an IRO compound according to the invention and a pharmaceutically acceptable carrier.

The invention further provides a method for inhibiting a TLR-mediated immune response in a vertebrate, or mammal, the method comprising administering to the mammal an IRO compound or composition according to the invention in a pharmaceutically effective amount. In some preferred embodiments, suppressing or inhibiting TLR stimulation comprises administering an IRO compound according to the invention, wherein the TLR is selected from TLR7 and TLR9.

The invention further provides a method for suppressing or inhibiting the activity of a TLR agonist comprising administering an IRO compound according to the invention, wherein the IRO compound is administered at the same time, prior to or after the TLR agonist. In preferred embodiments the TLR agonist is selected from agonists of TLR7 and TLR9.

The invention further provides a method for therapeutically treating a vertebrate, or mammal, having a disease mediated by TLR7 and/or TLR9, such method comprising administering to the mammal an IRO compound according to the invention in a pharmaceutically effective amount. In preferred embodiments, the disease is cancer, an autoimmune disease or disorder, airway inflammation, an inflammatory disease or disorder, infectious disease, malaria, Lyme disease, ocular infections, conjunctivitis, skin disorders, psoriasis, scleroderma, cardiovascular disease, atherosclerosis, chronic fatigue syndrome, sarcoidosis, transplant rejection, allergy, asthma or a disease caused by a pathogen. Preferred autoimmune diseases and disorders include without limitation lupus erythematosus, multiple sclerosis, type I diabetes mellitus, irritable bowel syndrome, Chron's disease, rheumatoid arthritis, septic shock, alopecia universalis, acute disseminated encephalomyelitis, Addison's disease, ankylosing spondylitis, antiphospholipid antibody syndrome, autoimmune hemolytic anemia, autoimmune hepatitis, Bullous pemphigoid, chagas disease, chronic obstructive pulmonary disease, coeliac disease, dermatomyositis, endometriosis, Goodpasture's syndrome, Graves' disease, Guillain-Barré syndrome, Hashimoto's disease, hidradenitis suppurativa, idiopathic thrombocytopenic purpura, interstitial cystitis, morphea, myasthenia gravis, narcolepsy, neuromyotonia, pemphigus, pernicious anaemia, polymyositis, primary biliary cirrhosis, schizophrenia, Sjögren's syndrome, temporal arteritis (also known as "giant cell arteritis"), vasculitis, vitiligo, vulvodynia, and Wegener's granulomatosis. Preferred inflammatory diseases and disorders include without limitation airway inflammation, asthma, autoimmune diseases, chronic inflammation, chronic prostatitis, glomerulonephritis, Behçet's disease, hypersensitivities, inflammatory bowel disease, reperfusion injury, rheumatoid arthritis, transplant rejection, ulcerative colitis, uveitis, conjunctivitis, and vasculitis.

The invention further provides a method for preventing cancer, autoimmune diseases or disorders, airway inflammation, inflammatory diseases or disorders, infectious disease, malaria, Lyme disease, ocular infections, conjunctivitis, skin disorders, psoriasis, scleroderma, cardiovascular disease, atherosclerosis, chronic fatigue syndrome, sarcoidosis, transplant rejection, allergy, asthma or a disease caused by a pathogen in a vertebrate, or mammal, such method comprising administering to the mammal an IRO compound according to the invention in a pharmaceutically effective amount. Preferred autoimmune diseases and disorders include without limitation lupus erythematosus, multiple sclerosis, type I diabetes mellitus, irritable bowel syndrome, Chron's disease, rheumatoid arthritis, septic shock, alopecia universalis, acute disseminated encephalomyelitis, Addison's disease, ankylosing spondylitis, antiphospholipid antibody syndrome, autoimmune hemolytic anemia, autoimmune hepatitis, Bullous pemphigoid, chagas disease, chronic obstructive pulmonary disease, coeliac disease, dermatomyositis, endometriosis, Goodpasture's syndrome, Graves' disease, Guillain-Barré syndrome, Hashimoto's disease, hidradenitis suppurativa, idiopathic thrombocytopenic purpura, interstitial cystitis, morphea, myasthenia gravis, narcolepsy, neuromyotonia, pemphigus, pernicious anaemia, polymyositis, primary biliary cirrhosis, schizophrenia, Sjögren's syndrome, temporal arteritis (also known as "giant cell arteritis"), vasculitis, vitiligo, vulvodynia, and Wegener's granulomatosis. Preferred inflammatory diseases and disorders include without limitation airway inflammation, asthma, autoimmune diseases, chronic inflammation, chronic prostatitis, glomerulonephritis, Behçet's disease, hypersensitivities, inflammatory bowel disease, reperfusion injury, rheumatoid arthritis, transplant rejection, ulcerative colitis, uveitis, conjunctivitis, and vasculitis.

In some preferred embodiments, the IRO compound according to the invention is administered in combination with one or more vaccines, antigens, antibodies, cytotoxic agents, allergens, antibiotics, antisense oligonucleotides, TLR agonists, TLR antagonists, peptides, proteins, gene therapy vectors, DNA vaccines, adjuvants, kinase inhibitors or co-stimulatory molecules or combinations thereof. In some preferred embodiments, the route of administration is parenteral, mucosal delivery, oral, sublingual, transdermal, topical, inhalation, intranasal, aerosol, intraocular, intratracheal, intrarectal, intragastric, vaginal, by gene gun, dermal patch or in eye drop or mouthwash form.

DETAILED DESCRIPTION OF THE PREFERRED EMBODIMENTS

Figure 1:
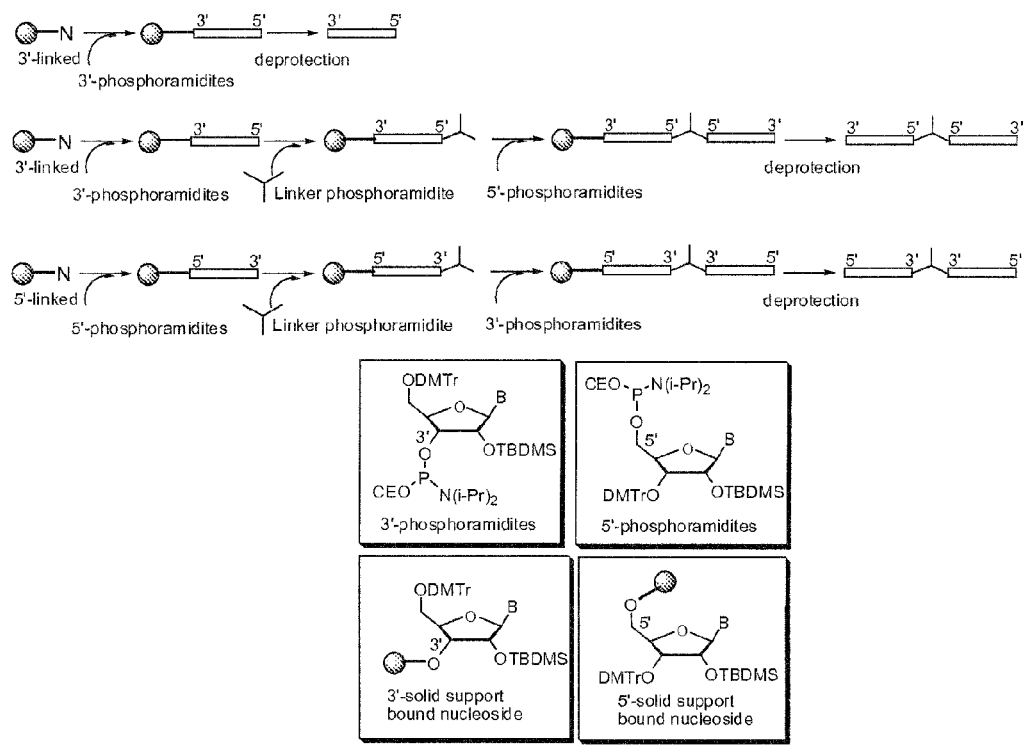
FIG. 1 is a synthetic scheme for the linear synthesis of immune regulatory compounds of the invention. DMTr=4,4'-dimethoxytrityl; CE=cyanoethyl.
Figure 2:
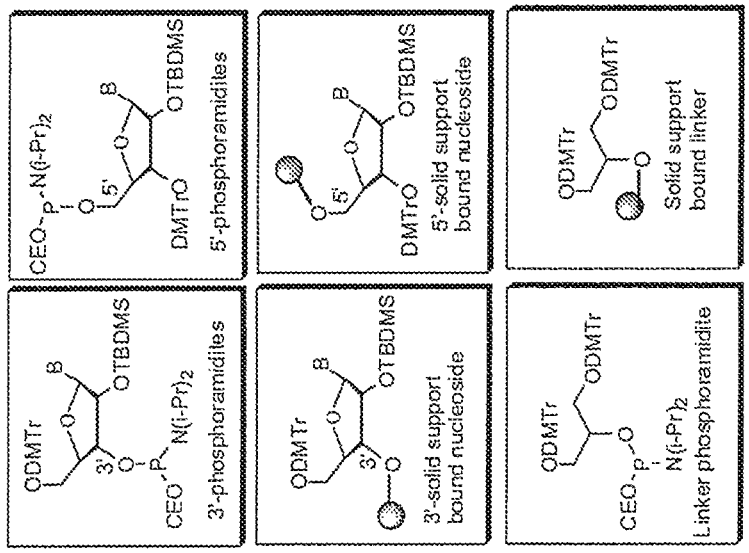
FIG. 2 is a synthetic scheme for the parallel synthesis of immune regulatory oligonucleotides of the invention. DMTr=4,4'-dimethoxytrityl; CE=cyanoethyl.
Figure 2:
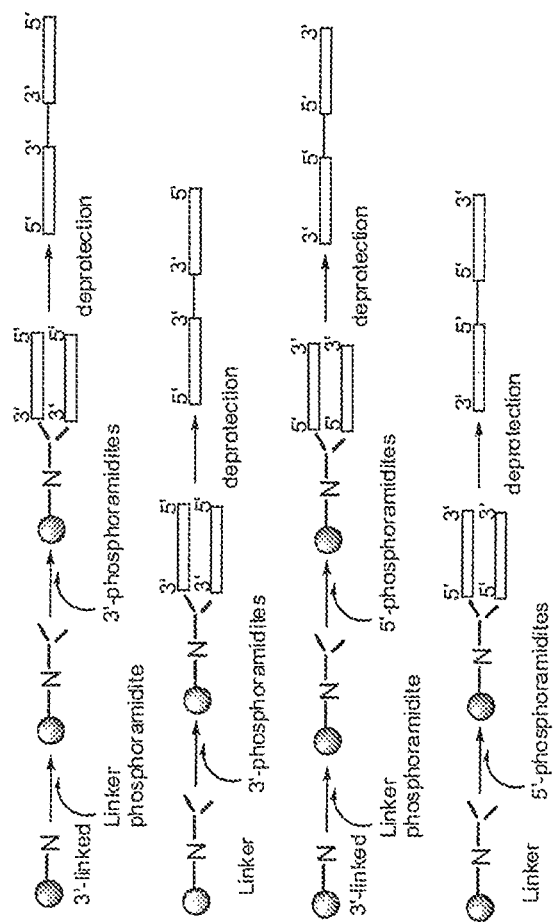

The present invention relates to the therapeutic use of novel oligonucleotide-based compounds as immune modulatory agents for immunotherapy applications. The invention provides novel oligonucleotide-based compounds that provide distinct immune inhibition profiles through their interaction with TLR7 and/or TLR9. Specifically, the invention provides Immune Regulatory Oligonucleotide (IRO) compounds as antagonists of toll-like receptors (TLRs) to inhibit and/or suppress a TLR-mediated immune response. These IROs have chemical modifications, and/or internucleotide linkages, and/or linkers between oligonucleotides that provide their inhibition or suppression of TLR7- and/or TLR9-mediated signaling in response to endogenous and/or exogenous TLR ligands or agonists. The references cited herein reflect the level of knowledge in the field and are hereby incorporated by reference in their entirety. Any conflicts between the teachings of the cited references and this specification shall be resolved in favor of the latter.

The invention further provides methods for suppressing an immune response caused by TLRs and can be used for immunotherapy applications such as, but not limited to, treatment of cancer, autoimmune disorders, asthma, respiratory allergies, food allergies, skin allergies, systemic lupus erythematosus (SLE), arthritis, pleurisy, chronic infections, inflammatory diseases, inflammatory bowel syndrome, sepsis, and bacteria, parasitic, and viral infections in adult and pediatric human and veterinary applications. Thus, the invention provides IRO compounds having optimal levels of immune modulatory effect for immunotherapy and methods for making and using such compounds. In addition, IRO compounds of the invention are useful in combination with, for example, vaccines, antigens, antibodies, allergens, chemotherapeutic agents (both chemotherapy and targeted therapies), and/or antisense oligonucleotides for prevention and treatment of diseases.

Definitions

The term "oligonucleotide" generally refers to a polynucleoside comprising a plurality of linked nucleoside units. Such oligonucleotides can be obtained from existing nucleic acid sources, including genomic or cDNA, but are preferably produced by synthetic methods. In preferred embodiments each nucleoside unit can encompass various chemical modifications and substitutions as compared to wild-type oligonucleotides, including but not limited to modified nucleoside base and/or modified sugar unit. Examples of chemical modifications are known to the person skilled in the art and are described, for example, in Uhlmann E et al. (1990) Chem. Rev. 90:543; "Protocols for Oligonucleotides and Analogs" Synthesis and Properties & Synthesis and Analytical Techniques, S. Agrawal, Ed, Humana Press, Totowa, USA 1993; and Hunziker, J. et al. (1995) Mod. Syn. Methods 7:331-417; and Crooke, S. et al. (1996) Ann. Rev. Pharm. Tox. 36:107-129. The nucleoside residues can be coupled to each other by any of the numerous known internucleoside linkages. Such internucleoside linkages include, without limitation, phosphodiester, phosphorothioate, phosphorodithioate, alkylphosphonate, alkylphosphonothioate, phosphotriester, phosphoramidate, siloxane, carbonate, carboalkoxy, acetamidate, carbamate, morpholino, borano, thioether, bridged phosphoramidate, bridged methylene phosphonate, bridged phosphorothioate, and sulfone internucleoside linkages. The term "oligonucleotide" also encompasses polynucleosides having one or more stereospecific internucleoside linkage (e.g., ($R_P$)- or ($S_P$)-phosphorothioate, alkylphosphonate, or phosphotriester linkages). As used herein, the terms "oligonucleotide" and "dinucleotide" are expressly intended to include polynucleosides and dinucleosides having any such internucleoside linkage, whether or not the linkage comprises a phosphate group. In certain preferred embodiments, these internucleoside linkages may be phosphodiester, phosphorothioate or phosphorodithioate linkages or combinations thereof.

The term "2'-substituted ribonucleoside" or "2'-substituted arabinoside" generally includes ribonucleosides or arabinonucleosides in which the hydroxyl group at the 2' position of the pentose moiety is substituted to produce a 2'-substituted or 2'-O-substituted ribonucleoside. In certain embodiments, such substitution is with a lower hydrocarbyl group containing 1-6 saturated or unsaturated carbon atoms, with a halogen atom, or with an aryl group having 6-10 carbon atoms, wherein such hydrocarbyl, or aryl group may be unsubstituted or may be substituted, for example, with halo, hydroxy, trifluoromethyl, cyano, nitro, acyl, acyloxy, alkoxy, carboxyl, carboalkoxy, or amino groups. Examples of 2'-O-substituted ribonucleosides or 2'-O-substituted-arabinosides include, without limitation 2'-amino, 2'-fluoro, 2'-allyl, 2'-O-alkyl and 2'-propargyl ribonucleosides or arabinosides, 2'-O-methylribonucleosides or 2'-O-methylarabinosides and 2'-O-methoxyethoxyribonucleosides or 2'-O-methoxyethoxyarabinosides.

The term "3'", when used directionally, generally refers to a region or position in a polynucleotide or oligonucleotide 3' (downstream) from another region or position in the same polynucleotide or oligonucleotide.

The term "5'", when used directionally, generally refers to a region or position in a polynucleotide or oligonucleotide 5' (upstream) from another region or position in the same polynucleotide or oligonucleotide.

The term "about" generally means that the exact number is not critical. Thus, the number of nucleoside residues in the oligonucleotides is not critical, and oligonucleotides having one or two fewer nucleoside residues, or from one to several additional nucleoside residues are contemplated as equivalents of each of the embodiments described above.

The term "agonist" generally refers to a substance that binds to a receptor of a cell and induces a response. An agonist often mimics the action of a naturally occurring substance such as a ligand.

The term "antagonist" generally refers to a substance that attenuates, inhibits or suppresses the effects of an agonist or ligand.

The term "adjuvant" generally refers to a substance which, when added to an immunogenic agent such as vaccine or antigen, enhances or potentiates an immune response to the agent in the recipient host upon exposure to the mixture.

The term "airway inflammation" generally includes, without limitation, asthma.

The term "allergen" generally refers to an antigen or antigenic portion of a molecule, usually a protein, which elicits an allergic response upon exposure to a subject. Typically the subject is allergic to the allergen as indicated, for instance, by the wheal and flare test or any method known in the art. A molecule is said to be an allergen even if only a small subset of subjects exhibit an allergic immune response upon exposure to the molecule.

The term "allergy" generally refers to an inappropriate immune response characterized by inflammation and includes, without limitation, food allergies and respiratory allergies.

The term "antigen" generally refers to a substance that is recognized and selectively bound by an antibody or by a T cell antigen receptor, resulting in induction of an immune response. Antigens may include but are not limited to peptides, proteins, nucleosides, nucleotides, and combinations thereof Antigens may be natural or synthetic and generally induce an immune response that is specific for that antigen.

The terms "autoimmune disease" and autoimmune disorder" generally refer to diseases or disorders in which "self" components undergo attack by the immune system.

The term "TLR-mediated disease" or TLR-mediated disorder" generally means any pathological condition for which activation of one or more TLRs is a contributing factor. Such conditions include but are not limited, cancer, autoimmune diseases or disorders, airway inflammation, inflammatory diseases or disorders, infectious diseases, skin disorders, allergy, asthma or diseases caused by a pathogen.

The term "physiologically acceptable" generally refers to a material that does not interfere with the effectiveness of an IRO compound or composition according to the invention and that is compatible with a biological system such as a cell, cell culture, tissue or organism. Preferably, the biological system is a living organism, such as a vertebrate, or mammal.

The term "carrier" generally encompasses any excipient, diluent, filler, salt, buffer, stabilizer, solubilizer, oil, lipid, lipid containing vesicle, microspheres, liposomal encapsulation or other material well known in the art for use in pharmaceutical formulations. It will be understood that the characteristics of the carrier, excipient or diluent will depend on the route of administration for a particular application. The preparation of pharmaceutically acceptable formulations containing these materials is described in, for example, *Remington's Pharmaceutical Sciences,* 18th Edition, ed. A. Gennaro, Mack Publishing Co., Easton, Pa., 1990.

The term "co-administration" generally refers to the administration of at least two different substances sufficiently close in time to modulate, suppress or inhibit an immune response. Co-administration refers to simultaneous administration, as well as temporally spaced order of up to several days apart, of at least two different substances in any order, either in a single dose or separate doses.

The term "complementary" generally means having the ability to hybridize to a nucleic acid. Such hybridization is ordinarily the result of hydrogen bonding between complementary strands, preferably to form Watson-Crick or Hoogsteen base pairs, although other modes of hydrogen bonding, as well as base stacking can also lead to hybridization.

The term an "effective amount" or a "sufficient amount" generally refers to an amount sufficient to affect a desired biological effect, such as beneficial results. Thus, an "effective amount" or "sufficient amount" will depend upon the context in which it is being administered. In the context of administering a compound or composition that modulates an immune response to a co-administered antigen, an effective amount of an IRO compound or composition according to the invention and antigen is an amount sufficient to achieve the desired modulation, inhibition or suppression as compared to the immune response obtained when the antigen is administered alone. An effective amount may be administered in one or more administrations.

The term "in combination with" generally means in the course of treating a disease or disorder in a patient, administering an IRO compound or composition according to the invention and an agent useful for treating the disease or disorder that does not diminish the immune inhibitory effect of the IRO compound or composition according to the invention. Such combination treatment may also include more than a single administration of an IRO compound or composition according to the invention and/or independently an agent. The administration of the IRO compound or composition according to the invention and/or the agent may be by the same or different routes.

The term "individual" or "subject" or "vertebrate" generally refers to a mammal. Mammals generally include, but are not limited to, humans, non-human primates, rats, mice, cats, dogs, horses, cattle, cows, pigs, sheep, and rabbits.

The term "kinase inhibitor" generally refers to molecules that antagonize or inhibit phosphorylation-dependent cell signaling and/or growth pathways in a cell. Kinase inhibitors may be naturally occurring or synthetic and include small molecules that have the potential to be administered as oral therapeutics. Kinase inhibitors have the ability to rapidly and specifically inhibit the activation of the target kinase molecules. Protein kinases are attractive drug targets, in part because they regulate a wide variety of signaling and growth pathways and include many different proteins. As such, they have great potential in the treatment of diseases involving kinase signaling, including cancer, cardiovascular disease, inflammatory disorders, diabetes, macular degeneration and neurological disorders. Examples of kinase inhibitors include sorafenib (Nexavar®), Sutent®, dasatinib, Dasatinib™, Zactima™, Tykerb™ and STI571.

The term "nucleoside" generally refers to compounds consisting of a sugar, usually ribose or deoxyribose, and a purine or pyrimidine base.

The term "nucleotide" generally refers to a nucleoside comprising a phosphate group attached to the sugar.

As used herein, the term "pyrimidine nucleoside" refers to a nucleoside wherein the base component of the nucleoside is a pyrimidine base (e.g., cytosine (C) or thymine (T) or Uracil (U)). Similarly, the term "purine nucleoside" refers to a nucleoside wherein the base component of the nucleoside is a purine base (e.g., adenine (A) or guanine (G)).

The terms "analog" or "derivative" can be used interchangeable to generally refer to any purine and/or pyrimidine nucleotide or nucleoside that has a modified base and/or sugar. A modified base is a base that is not guanine, cytosine, adenine, thymine or uracil. A modified sugar is any sugar that is not ribose or 2'deoxyribose and can be used in the backbone for an oligonucleotide.

The term "inhibiting" or "suppressing" generally refers to a decrease in or a prevention of a response or qualitative difference in a response, which could otherwise arise from eliciting and/or stimulation of a response.

The term "non-nucleotide linker" generally refers to any linkage or moiety that can link or be linked to the oligonucleotides other than through a phosphorous-containing linkage. Preferably such linker is from about 2 angstroms to about 200 angstroms in length.

The term "nucleotide linkage" generally refers to a direct 3'-5' linkage that directly connects the 3' and 5' hydroxyl groups of two nucleosides through a phosphorous-containing linkage.

The terms "oligonucleotide motif" means an oligonucleotide sequence, including a dinucleotide selected from CpG, C*pG, C*pG* or CpG*. The terms CpG, C*pG, C*pG* and CpG* refer to oligonucleotide motifs that are immune stimulatory wherein C is cytosine, C* is a cytosine analog or derivative, G is a guanine and G* is a guanine analog or derivative.

An "oligonucleotide motif that would be immune stimulatory, but for one or more modifications" means an oligonucleotide motif which is immune stimulatory in a parent oligonucleotide, but not in a derivative oligonucleotide, wherein the derivative oligonucleotide is based upon the parent oligonucleotide, but has one or more modifications. In other words, an "oligonucleotide motif that would be immune stimulatory, but for one or more modifications" refers to a TLR9-inducing moiety that would have TLR9 agonistic activity but for that fact that it has been functionally blocked or inhibited from inducing TLR9 mediated immune response through modification(s) of the TLR9-inducing moiety itself and/or by one or more chemical modification within the oligonucleotide based compound. Modifications that inhibit the activity of a TLR9-inducing moiety include, but not limited to, 2'-OMe-ribonucleosides, 3'-OMe-ribonucleosides, 3-nitropyrrole, 5-nitroindole, dU, β-L-deoxynucleosides, α-deoxynucleosides, abasic nucleoside, propanediol linker, amino linker, isopropoxyl, glycerol linker, 2'-5'-DNA, 2'-5' RNA, and P-Me DNA.

The term "treatment" generally refers to an approach intended to obtain a beneficial or desired results, which may include alleviation of symptoms and/or delaying and/or ameliorating the progression of a disease or disorder.

Certain IROs according to the invention are shown in Table 2. In this table, the IRO compounds have all phosphorothioate (PS) linkages, except where indicated with 'o'. Except where indicated, all nucleotides are deoxyribonucleotides.

TABLE 2

| IRO compound # | Sequence/Structure/SEQ ID NO |
|---|---|
| 1 | 5'-UGUCG1TTCT-X1-TCTTG1CUGU-5' <br> 5'-SEQ ID NO 1-3'-X1-3'-SEQ ID NO 1-5' |
| 2 | 5'-UGUCG1TTC-X1-CTTG1CUGU-5' <br> 5'-SEQ ID NO 2-3'-X1-3'-SEQ ID NO 2-5' |
| 3 | 5'-UGUCG1TT-X1-TTG1CUGU-5' <br> 5'-SEQ ID NO 3-3'-X1-3'-SEQ ID NO 3-5' |
| 4 | 5'-UGUCoG1TTCTo-Z-oTCTTG1oCUGU-5' <br> 5'-SEQ ID NO 1-3'-Z-3'-SEQ ID NO 1-5' |
| 5 | 5'-GUCG1TTCTT-Z-TTCTTG1CUG-5' <br> 5'-SEQ ID NO 4-3'-Z-3'-SEQ ID NO 4-5' |
| 6 | 5'-UGUCG2TTCT-Z-TCTTG2CUGU-5' <br> 5'-SEQ ID NO 5-3'-Z-3'-SEQ ID NO 5-5' |
| 7 | 5'-UGUCG1TTCT-X4-TCTTG1CUGU-5' <br> 5'-SEQ ID NO 1-3'-X4-3'-SEQ ID NO 1-5' |
| 8 | 5'-UGUCG1TTC-X4-CTTG1CUGU-5' <br> 5'-SEQ ID NO 2-3'-X4-3'-SEQ ID NO 2-5' |
| 9 | 5'-UGUCoG1TTCTo-X4-oTCTTG1oCUGU-5' <br> 5'-SEQ ID NO 1-3'-X4-3'-SEQ ID NO 1-5' |
| 10 | 5'-GUCG1TTCTT-X4-TTCTTG1CUG-5' <br> 5'-SEQ ID NO 4-3'-X4-3'-SEQ ID NO 4-5' |
| 11 | 5'-UGUCG1TT-X4-TTG1CUGU-5' <br> 5'-SEQ ID NO 3-3'-X4-3'-SEQ ID NO 3-5' |
| 12 | 5'-UGUCG1TTC-X5-CTTG1CUGU-5' <br> 5'-SEQ ID NO 2-3'-X5-3'-SEQ ID NO 2-5' |
| 13 | 5'-UGUCG2TTC-X5-CTTG2CUGU-5' <br> 5'-SEQ ID NO 6-3'-X5-3'-SEQ ID NO 6-5' |
| 14 | 5'-UGUCG1TTC-X6-CTTG1CUGU-5' <br> 5'-SEQ ID NO 2-3'-X6-3'-SEQ ID NO 2-5' |
| 15 | 5'-UGUCG2TTC-X6-CTTG2CUGU-5' <br> 5'-SEQ ID NO 6-3'-X6-3'-SEQ ID NO 6-5' |
| 16 | 5'-UGUCG1TTCT-X7-TCTTG1CUGU-5' <br> 5'-SEQ ID NO 1-3'-X7-3'-SEQ ID NO 1-5' |
| 17 | 5'-UGUCG2TTCT-X7-TCTTG2CUGU-5' <br> 5'-SEQ ID NO 5-3'-X7-3'-SEQ ID NO 5-5' |
| 18 | 5'-UGUCG1TTC-X7-CTTG1CUGU-5' <br> 5'-SEQ ID NO 2-3'-X7-3'-SEQ ID NO 2-5' |
| 19 | 5'-TGUCG1TTCT-X-TCTTG1CUGT-5' <br> 5'-SEQ ID NO 7-3'-X-3'-SEQ ID NO 7-5' |
| 20 | 5'-CTTGUCG1TTC-X-TCTTG1CUGTTC-5' <br> 5'-SEQ ID NO 8-3'-X-3'-SEQ ID NO 8-5' |
| 21 | 5'-TTGUCG1TTC-X-CTTG1CUGTT-5' <br> 5'-SEQ ID NO 9-3'-X-3'-SEQ ID NO 9-5' |
| 22 | 5'-CTTTGUCG1TTC-X-CTTG1CUGTTTC-5' <br> 5'-SEQ ID NO 10-3'-X-3'-SEQ ID NO 10-5' |
| 23 | 5'-TGUCG1TTCT-X7-TCTTG1CUGT-5' <br> 5'-SEQ ID NO 7-3'-X7-3'-SEQ ID NO 7-5' |
| 24 | 5'-TTGUCG1TTC-X7-CTTG1CUGTT-5' <br> 5'-SEQ ID NO 9-3'-X7-3'-SEQ ID NO 9-5' |
| 25 | 5'-GUCG1TTCTT-Z-TTCTTG1CUG-5' <br> 5'-SEQ ID NO 4-3'-Z-3'-SEQ ID NO 4-5' |
| 26 | 5'-TGUCG1TTCA-X-ACTTG1CUGT-5' <br> 5'-SEQ ID NO 11-3'-X-3'-SEQ ID NO 11-5' |
| 27 | 5'-TCTGACG1TTCT-X-TCTTG1CAGTCT-5' <br> 5'-SEQ ID NO 12-3'-X1-3'-SEQ ID NO 12-5' |
| 28 | 5'-TCTGACG2TTCT-X-TCTTG2CAGTCT-5' <br> 5'-SEQ ID NO 13-3'-X-3'-SEQ ID NO 13-5' |
| 29 | 5'-TTGUCG1TTA-X-ATTG1CUGTT-5' <br> 5'-SEQ ID NO 14-3'-X-3'-SEQ ID NO 14-5' |
| 30 | 5'-CTCTGUCG1TTA-X-ATTG1CUGTCTC-5' <br> 5'-SEQ ID NO 15-3'-X-3'-SEQ ID NO 15-5' |
| 31 | 5'-TGTC*GTTCT-X-TCTTGC*TGT-5' <br> 5'-SEQ ID NO 16-3'-X-3'-SEQ ID NO 16-5' |
| 32 | 5'-TGTCGTTCT-X-TCTTGCTGT-5' <br> 5'-SEQ ID NO 17-3'-X-3'-SEQ ID NO 17-5' |
| 33 | 5'-TGTC*GTTCT-X-TCTTGC*TGT-5' <br> 5'-SEQ ID NO 69-3'-X-3'-SEQ ID NO 69-5' |
| 34 | 5'-TGTCGTTCT-X-TCTTGCTGT-5' <br> 5'-SEQ ID NO 18-3'-X-3'-SEQ ID NO 18-5' |
| 35 | 5'-UGUCG1ACAT-X-TACAG1CUGU-5' <br> 5'-SEQ ID NO 19-3'-X-3'-SEQ ID NO 19-5' |
| 36 | 5'-UGUCG1TTC-X-CTTG1CUGU-5' <br> 5'-SEQ ID NO 2-3'-X-3'-SEQ ID NO 2-5' |
| 37 | 5'-UGUCG1TT-X-TTG1CUGU-5' <br> 5'-SEQ ID NO 3-3'-X-3'-SEQ ID NO 3-5' |
| 38 | 5'-UoGUCG1TToCTo-X-oTCoTTG1CUGoU-5' <br> 5'-SEQ ID NO 1-3'-X-3'-SEQ ID NO 1-5' |
| 39 | 5'-UoGoUCG1TTCTo-X-oTCTTG1CUoGoU-5' <br> 5'-SEQ ID NO 1-3'-X-3'-SEQ ID NO 1-5' |

TABLE 2-continued

| IRO compound # | Sequence/Structure/SEQ ID NO |
|---|---|
| 40 | 5'-UGACG1TTCT-X-TCTTG1CAGU-5'<br>5'-SEQ ID NO 20-3'-X-3'-SEQ ID NO 20-5' |
| 41 | 5'-UGUCG1ACAT-Z-TACAG1CUGU-5'<br>5'-SEQ ID NO 19-3'-Z-3'-SEQ ID NO 19-5' |
| 42 | 5'-UGUCG1TTCT-Z-TCTTG1CUGU-5'<br>5'-SEQ ID NO 1-3'-Z-3'-SEQ ID NO 1-5' |
| 43 | 5'-UGUCG1TTC-Z-CTTG1CUGU-5'<br>5'-SEQ ID NO 2-3'-Z-3'-SEQ ID NO 2-5' |
| 44 | 5'-UGUCG1TT-Z-TTG1CUGU-5'<br>5'-SEQ ID NO 3-3'-Z-3'-SEQ ID NO 3-5' |
| 45 | 5'-UGUC*GTTCT-X-TCTTGC*UGU-5'<br>5'-SEQ ID NO 21-3'-X-3'-SEQ ID NO 21-5' |
| 46 | 5'-T^G^T^C*GTTCT-X-TCTTGC*T^G^T^-5'<br>5'-SEQ ID NO 22-3'-X-3'-SEQ ID NO 22-5' |
| 47 | 5'-UGUC*GTTCT-X-TCTTGC*UGU-5'<br>5'-SEQ ID NO 23-3'-X-3'-SEQ ID NO 23-5' |
| 48 | 5'-T^G^T^C*GTTCT-X-TCTTGC*T^G^T^-5'<br>5'-SEQ ID NO 24-3'-X-3'-SEQ ID NO 24-5' |
| 49 | 5'-UGUCG1ACAT-X1-TACAG1CUGU-5'<br>5'-SEQ ID NO 19-3'-X1-3'-SEQ ID NO 19-5' |
| 50 | 5'-UGACG2TTCT-X-TCTTG2CAGU-5'<br>5'-SEQ ID NO 25-3'-X-3'-SEQ ID NO 25-5' |
| 51 | 5'-TCTGUCG1TTCT-X-TCTTG1CUGTCT-5'<br>5'-SEQ ID NO 26-3'-X-3'-SEQ ID NO 26-5' |
| 52 | 5'-TCTGUCG2TTCT-X-TCTTG2CUGTCT-5'<br>5'-SEQ ID NO 27-3'-X-3'-SEQ ID NO 27-5' |
| 53 | 5'-UGUCG2TTCT-X-TCTTG2CUGU-5'<br>5'-SEQ ID NO 5-3'-X-3'-SEQ ID NO 5-5' |
| 54 | 5'-UGUCG2TT-Z-TTG2CUGU-5'<br>5'-SEQ ID NO 28-3'-Z-3'-SEQ ID NO 28-5' |
| 55 | 5'-TUGUCG1TTC-Z-CTTG1CUGUT-5'<br>5'-SEQ ID NO 29-3'-Z-3'-SEQ ID NO 29-5' |
| 56 | 5'-CTUGUCG1TT-Z-TTG1CUGUTC-5'<br>5'-SEQ ID NO 30-3'-Z-3'-SEQ ID NO 30-5' |
| 57 | 5'-UCG1TTCTTC-Z-CTTCTTG1CU-5'<br>5'-SEQ ID NO 31-3'-Z-3'-SEQ ID NO 31-5' |
| 58 | 5'-CTATCTGAC*GTTCTCTGT-3'<br>5'-SEQ ID NO 32-3' |
| 59 | 5'-CTATCTGACGTTCTCTGT-3'<br>5'-SEQ ID NO 33-3' |
| 60 | 5'-CTATCTGAC*GTTCTCTGT-3'<br>5'-SEQ ID NO 34-3' |
| 61 | 5'-CTATCTGACGTTCTCTGT-3'<br>5'-SEQ ID NO 35-3' |
| 62 | 5'-CTATCTG^A^CGTTCTCTGT-3'<br>5'-SEQ ID NO 36-3' |
| 63 | 5'-CTATCTGUC*GTTCTCTGT-3'<br>5'-SEQ ID NO 37-3' |
| 64 | 5'-CTATCTGUCGTTCTCTGT-3'<br>5'-SEQ ID NO 38-3' |
| 65 | 5'-CTATCTGUC*GTTCTCTGT-3'<br>5'-SEQ ID NO 39-3' |
| 66 | 5'-CTATCTGUCGTTCTCTGT-3'<br>5'-SEQ ID NO 40-3' |
| 67 | 5'-CTTGUC*G1TTCT-X-TCTTG1C*UGTTC-5'<br>5'-SEQ ID NO 41-3'-X-3'-SEQ ID NO 41-5' |
| 68 | 5'-CTATCTGUC*G1TTCTCTGU-3'<br>5'-SEQ ID NO 42-3' |
| 69 | 5'-UGUCG1TTCT-X-TCTTG1CUGU-5'<br>5'-SEQ ID NO 1-3'-X-3'-SEQ ID NO 1-5' |
| 70 | 5'-TGUC*G1TTCT-X-TCTTG1C*UGT-5'<br>5'-SEQ ID NO 43-3'-X-3'-SEQ ID NO 43-5' |
| 71 | 5'-CTTTGUC*G1TTC-X-CTTG1C*UGTTTC-5'<br>5'-SEQ ID NO 44-3'-X-3'-SEQ ID NO 44-5' |
| 72 | 5'-GUC*G1TTCTT-X-TTCTTG1C*UG-5'<br>5'-SEQ ID NO 45-3'-X-3'-SEQ ID NO 45-5' |
| 73 | 5'-TGUC*G1TTCA-X-ACTTG1C*UGT-5'<br>5'-SEQ ID NO 46-3'-X-3'-SEQ ID NO 46-5' |
| 74 | 5'-CTTGUC*G1TTCT-X1-TCTTG1C*UGTTC-5'<br>5'-SEQ ID NO 41-3'-X1-3'-SEQ ID NO 41-5' |
| 75 | 5'-CTTGUC*G2TTCT-X-TCTTG2C*UGTTC-5'<br>5'-SEQ ID NO 47-3'-X-3'-SEQ ID NO 47-5' |
| 76 | 5'-CTTGUC*G1TTC-X5-CTTG1C*UGTTC-5'<br>5'-SEQ ID NO 48-3'-X5-3'-SEQ ID NO 48-5' |
| 77 | 5'-CTTGUC*G1TTCT-X7-TCTTG1C*UGTTC-5'<br>5'-SEQ ID NO 41-3'-X7-3'-SEQ ID NO 41-5' |

TABLE 2-continued

| IRO compound # | Sequence/Structure/SEQ ID NO |
|---|---|
| 78 | 5'-CTTTGUC*oG1TTC-X-CTTG1oC*UGTTC-5'<br>5'-SEQ ID NO 44-3'-X-3'-SEQ ID NO 44-5' |
| 79 | 5'-CTTTGoUC*oG1TTC-X-CTTG1oC*UoGTTTC-5'<br>5'-SEQ ID NO 44-3'-X-3'-SEQ ID NO 44-5' |
| 80 | 5'-CTTGUC*oG1TTCT-X-TCTTG1oC*UGTTC-5'<br>5'-SEQ ID NO 41-3'-X-3'-SEQ ID NO 41-5' |
| 81 | 5'-CTTGoUC*oG1TTCT-X-TCTTG1oC*UoGTTC-5'<br>5'-SEQ ID NO 41-3'-X-3'-SEQ ID NO 41-5' |
| 82 | 5'-CTGUC*oG1TTCTT-X-TTCTTG1oC*UGTC-5'<br>5'-SEQ ID NO 49-3'-X-3'-SEQ ID NO 49-5' |
| 83 | 5'-CTGoUC*oG1TTCTT-X-TTCTTG1oC*UoGTC-5'<br>5'-SEQ ID NO 49-3'-X-3'-SEQ ID NO 49-5' |
| 84 | 5'-UGUC*G1TTCT-X1-TCTTG1C*UGU-5'<br>5'-SEQ ID NO 50-3'-X1-3'-SEQ ID NO 50-5' |
| 85 | 5'-UGUC*G2TTCT-X-TCTTG2C*UGU-5'<br>5'-SEQ ID NO 51-3'-X-3'-SEQ ID NO 51-5' |
| 86 | 5'-UGUC*G1TTC-X5-CTTG1C*UGU-5'<br>5'-SEQ ID NO 52-3'-X5-3'-SEQ ID NO 52-5' |
| 87 | 5'-UGUC*G1TTCT-X7-TCTTG1C*UGU-5'<br>5'-SEQ ID NO 50-3'-X7-3'-SEQ ID NO 50-5' |
| 88 | 5'-CTATCTGUC*G1TTCTCTGT-3'<br>5'-SEQ ID NO 53-3' |
| 89 | 5'-CTATCTGUC*G1TTCTCTGT-3'<br>5'-SEQ ID NO 54-3' |
| 90 | 5'-TGAC*G1TTCT-X-TCTTG1C*AGT-5'<br>5'-SEQ ID NO 55-3'-X-3'-SEQ ID NO 55-5' |
| 91 | 5'-CTTGAC*G1TTCT-X-TCTTG1C*AGTTC-5'<br>5'-SEQ ID NO 56-3'-X-3'-SEQ ID NO 56-5' |
| 92 | 5'-CTTTGAC*G1TTC-X-CTTG1C*AGTTTC-5'<br>5'-SEQ ID NO 57-3'-X-3'-SEQ ID NO 57-5' |
| 93 | 5'-GAC*G1TTCTT-X-TTCTTG1C*AG-5'<br>5'-SEQ ID NO 58-3'-X-3'-SEQ ID NO 58-5' |
| 94 | 5'-TGAC*G1TTCA-X-ACTTG1C*AGT-5'<br>5'-SEQ ID NO 59-3'-X-3'-SEQ ID NO 59-5' |
| 95 | 5'-CTTGAC*G1TTCT-X1-TCTTG1C*AGTTC-5'<br>5'-SEQ ID NO 56-3'-X1-3'-SEQ ID NO 56-5' |
| 96 | 5'-CTTGAC*G2TTCT-X-TCTTG2C*AGTTC-5'<br>5'-SEQ ID NO 60-3'-X-3'-SEQ ID NO 60-5' |
| 97 | 5'-CTTGAC*G1TTC-X5-CTTG1C*AGTTC-5'<br>5'-SEQ ID NO 61-3'-X5-3'-SEQ ID NO 61-5' |
| 98 | 5'-CTTGAC*G1TTCT-X7-TCTTG1C*AGTTC-5'<br>5'-SEQ ID NO 56-3'-X7-3'-SEQ ID NO 56-5' |
| 99 | 5'-CTTTGAC*oG1TTC-X-CTTG1oC*AGTTTC-5'<br>5'-SEQ ID NO 57-3'-X-3'-SEQ ID NO 57-5' |
| 100 | 5'-CTTTGoAC*oG1TTC-X-CTTG1oC*AoGTTTC-5'<br>5'-SEQ ID NO 57-3'-X-3'-SEQ ID NO 57-5' |
| 101 | 5'-CTTGAC*oG1TTCT-X-TCTTG1oC*AGTTC-5'<br>5'-SEQ ID NO 56-3'-X-3'-SEQ ID NO 56-5' |
| 102 | 5'-CTTGoAC*oG1TTCT-X-TCTTG1oC*AoGTTC-5'<br>5'-SEQ ID NO 56-3'-X-3'-SEQ ID NO 56-5' |
| 103 | 5'-CTGAC*oG1TTCTT-X-TTCTTG1oC*AGTC-5'<br>5'-SEQ ID NO 62-3'-X-3'-SEQ ID NO 62-5' |
| 104 | 5'-CTGoAC*oG1TTCTT-X-TTCTTG1oC*AoGTC-5'<br>5'-SEQ ID NO 62-3'-X-3'-SEQ ID NO 62-5' |
| 105 | 5'-UGAC*G1TTCT-X-TCTTG1C*AGU-5'<br>5'-SEQ ID NO 63-3'-X-3'-SEQ ID NO 63-5' |
| 106 | 5'-UGAC*G1TTCT-X1-TCTTG1C*AGU-5'<br>5'-SEQ ID NO 63-3'-X1-3'-SEQ ID NO 63-5' |
| 107 | 5'-UGAC*G2TTCT-X-TCTTG2C*AGU-5'<br>5'-SEQ ID NO 64-3'-X-3'-SEQ ID NO 64-5' |
| 108 | 5'-UGAC*G1TTC-X5-CTTG1C*AGU-5'<br>5'-SEQ ID NO 65-3'-X5-3'-SEQ ID NO 65-5' |
| 109 | 5'-UGAC*G1TTCT-X7-TCTTG1C*AGU-5'<br>5'-SEQ ID NO 63-3'-X7-3'-SEQ ID NO 63-5' |
| 110 | 5'-CTATCTGAC*G1TTCTCTGT-3'<br>5'-SEQ ID NO 66-3' |

15

TABLE 2-continued

| IRO compound # | Sequence/Structure/SEQ ID NO |
|---|---|
| 111 | 5'-CTATCTGAC*G1TTCTCTGT-3'<br>5'-SEQ ID NO 67-3' |
| 112 | 5'-CTATCTGAC*G1TTCTCTGU-3'<br>5'-SEQ ID NO 68-3' |

G1 = 7-deaza-dG;
G2 = AraG;
C* = 5-Me-dC;
C* = 2'-O-Me-5-Me-C;
A^/G^/T^/G^ = 2'-0-(2-methoxyethyl)-ribonucelotides;
X = Glycerol Linker (also known as 1,2,3-Propanetriol Linker);
X1 = 1,2,4-Butanetriol Linker;
Z = 1,3,5-Pentanetriol Linker;
X4 = 3-Trimethylamino-1,2-propanediol Linker;
X5 = Bis-1,5-O-(3'-thymidyl)-1,3,5-pentanetriol Linker;
X6 = Bis-1,5-O-[3'-(1,2-dideoxy-D-ribosyl)]-1,3-5-pentanetriol Linker;
X7 = 3-(2-Hydroxyethyl)-1,5-pentanediol Linker;
G/U/A/C = 2'-O-Me-ribonucleotides;
o = Phosphodiester linkage.

In a first aspect, the invention provides immune regulatory oligonucleotide (IRO) compounds. The term "IRO" refers to an immune regulatory oligonucleotide-based compound that is an antagonist for TLR7- and/or TLR9, wherein the compound comprises an oligonucleotide motif and at least one modification, wherein the oligonucleotide motif would be immune stimulatory but for the one or more modifications that functionally block or inhibit the activity of the oligonucleotide motif, provided that the compound contains less than 4 consecutive guanosine nucleotides and preferably less than 3 consecutive guanosine nucleotides. Such modifications may be in the oligonucleotide 5' terminus, in the 5' sequence flanking the oligonucleotide motif, and/or within the immune stimulatory oligonucleotide motif. These modifications result in an IRO compound that antagonize, inhibit, suppresses or prevent TLR7- and/or TLR9-mediated immune stimulation. Such modifications can be to the bases, sugar residues and/or the phosphate backbone of the nucleotides/nucleosides flanking the immune stimulatory oligonucleotide motif or within such oligonucleotide motif.

The general structure of the IRO compound has the structure 5'-$N_m$—$N_3N_2N_1CGN^1N^2N^3$—$N^m$-3' (SEQ ID NO: 70) wherein CG is an oligonucleotide motif selected from CpG, C*pG, C*pG* or CpG* wherein C is cytosine, C* is a cytosine analog or derivative, G is a guanine and G* is a guanine analog or derivative; $N_1$—$N_3$, at each occurrence, is independently a nucleotide or nucleotide derivative; $N^1$—$N^3$, at each occurrence, is independently a nucleotide or nucleotide derivative; $N_m$ and Nm, at each occurrence, is independently a nucleotide, nucleotide derivative or non-nucleotide linker; provided that at least one of $N_1$, $N_2$, and $N_3$ and/or C and/or G of the oligonucleotide motif is a nucleotide derivative that functionally blocks or inhibits the activity of the oligonucleotide motif; and further provided that the compound contains less than 4 consecutive guanosine nucleotides and preferably less than 3 consecutive guanosines, wherein the immune stimulatory activity of the oligonucleotide motif is antagonized, inhibited, suppressed or prevented by the nucleotide derivative; and wherein m is a number from 0 to about 30.

In preferred embodiments, $N_1$ is a nucleotide derivative that functionally blocks or inhibits the activity of the oligonucleotide motif. In preferred embodiments $N_1$ and $N_2$, or $N_1$ and $N_3$, or $N_2$ and $N_3$, or $N_1$, $N_2$ and $N_3$ are nucleotide derivatives that functionally blocks or inhibits the activity of the oligonucleotide motif.

16

In preferred embodiments the IRO compound is not an antisense oligonucleotide.

In certain embodiments of the invention, the IRO compound may comprise at least two oligonucleotides (for example 2, 3, 4, 5 or 6 oligonucleotides), wherein at least two oligonucleotides are covalently linked via a direct nucleotide to nucleotide linkage at their 3' ends through the 3' positions of the sugars or through a modified sugar or modified nucleobase or via a non-nucleotide linker at their 3' ends through the 3' positions of the sugars or through a modified sugar or modified nucleobase. In preferred aspects of this embodiment, at least one of oligonucleotides of the IRO compound has the structure 5'-$N_m$—$N_3N_2N_1CGN^1N^2N^3$—$N^m$-3' (SEQ ID NO: 70), wherein $N_m$, $N_1$, $N_2$, $N_3$, C, G, $N^1$, $N^2$, $N^3$ and $N^m$ are as described above for the general structure of the IRO compound. In more preferred aspects of this embodiment, at least two of the oligonucleotides of the IRO compound have the structure 5'-$N_m$—$N_3N_2N_1CGN^1N^2N^3$—$N^m$-3' (SEQ ID NO: 70), wherein $N_m$, $N_1$, $N_2$, $N_3$, C, G, $N^1$, $N^2$, $N^3$ and $N^m$ are as described above for the general structure of the IRO compound. Such an IRO compound may have the structure 540 -$N_m$ -$N_3N_2N_1CGN^1N^2N^3N^m$-3'-X-3'-$N^m N^3 N^2 N^1 GCN_1N_2N_3 N_m$-5' (5'-SEQ ID NO: 70-3'-X-3'-SEQ ID NO: 70-5'), wherein X is a nucleotide linkage or a non-nucleotide linker and $N_m$, $N_1$, $N_2$, $N_3$, C, G, $N^1$, $N^2$, $N^3$ and $N^m$ are as described above for the general structure of the IRO compound.

In certain embodiments of the invention, the IRO compound that is an antagonist of TLR7 and/or TLR9 has the structure 5-$N_pN_3N_2N_1C*G*N^1N^2N^3N^zN^4N_5$- 3' (SEQ ID NO: 71), wherein C*G* is an oligonucleotide motif wherein C* is 5-Me-dC, and G* is 7-deaza-dG; $N_1$-$N_2$, at each occurrence, is independently a 2'-O-Me-ribonucleotide; $N_3$, at each occurrence, is independently a nucleotide or nucleotide derivative; $N^1$-$N^3$, at each occurrence, is independently a nucleotide or nucleotide derivative; $N_p$ and $N^z$, at each occurrence, is independently a nucleotide or nucleotide derivative; $N^4$—$N^5$, at each occurrence, is independently a 2'-O-Me-ribonucleotide; p is a number from 0 to about 30 and z is a number from 0 to about 30; provided that the compound contains less than 3 consecutive guanosines. In certain embodiments p and z are independently a number from 1 to about 20. In certain embodiments p and z are independently a number from 2 to about 15. In certain embodiments p and z are independently a number from 3 to about 10.

In certain embodiments of the invention, the IRO compound that is an antagonist of TLR7 and/or TLR9 has the structure 5-$N_pN_3N_2N_1C*G*N^1N^2N^3N^zN^4N^5$-3' (SEQ ID NO: 72), wherein C*G* is an oligonucleotide motif wherein C* is 5-Me-dC, and G* is 7-deaza-dG; $N_1$-$N_2$, at each occurrence, is independently a 2'-O-Me-ribonucleotide; $N_3$, at each occurrence, is independently a nucleotide; $N^1$-$N^3$, at each occurrence, is independently a nucleotide; $N_p$ and $N^z$, at each occurrence, is independently a nucleotide; $N^4$-$N^5$ at each occurrence, is independently a 2'-O-Me-ribonucleotide; p is 5 and z is 3; provided that the compound contains less than 3 consecutive guanosines. Alternatively, SEQ ID NO: 72 can be written as 5'-NNNNN$N_3N_2N_1$C*G*$N^1N^2N^3$NNNN$^4N^5$-3'.

In preferred embodiments, two oligonucleotides having the structure 5'-$N_m$—$N_3N_2N_1CGN^1N^2N^3$—$N^m$-3' (SEQ ID NO: 70) are covalently linked via a direct nucleotide to nucleotide linkage at their 3' ends through the 3' positions of the sugars or through a modified sugar or modified nucleobase or via a non-nucleotide linker at their 3' ends through the 3' positions of the sugars or through a modified sugar or modified nucleobase. In preferred aspects of this embodiment, the IRO compound has the structure 5'-$N_m$—

$N_3N_2N_1CGN^1N^2N^3$—$N^{m}$-3'-X-3'-$N^{m}N_3N_2N^1GCN_1N_2N_3$-$N_m$-5' (5'-SEQ ID NO: 70-3'-X-3'-SEQ ID NO: 70-5'), wherein X is a nucleotide linkage or a non-nucleotide linker and $N_m$, $N_1$, $N_2$, $N_3$, C, G, $N^1$, $N^2$, $N^3$ and $N^{m}$ are as described above for the general structure of the IRO compound. In preferred embodiments, the two oligonucleotides are covalently linked directly via a nucleotide linkage. In more preferred embodiments, the two oligonucleotides are covalently linked via a non-nucleotide linker.

As a non-limiting example, the non-nucleotide linker covalently linking the two oligonucleotides may be attached to the 3'-hydroxyl of the sugar. In such embodiments, the linker comprises a functional group, which is attached to the 3'-hydroxyl by means of a phosphate-based linkage like, for example, phosphodiester, phosphorothioate, phosphorodithioate, methylphosphonate, or by a non-phosphate-based linkage. Possible sites of conjugation for the linker to the 3' end of the oligonucleotide are indicated in Formula I, below, wherein B represents a heterocyclic base and wherein the arrow pointing to P indicates any attachment to phosphorous.

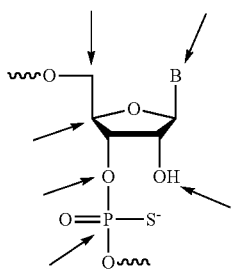

Formula I

In certain embodiments according to this aspect of the invention, the non-nucleotide linker is a small molecule, macromolecule or biomolecule, including, without limitation, polypeptides, antibodies, lipids, antigens, allergens, and oligosaccharides. In certain other embodiments, the non-nucleotide linker is a small molecule. For purposes of the invention, a small molecule is an organic moiety having a molecular weight of less than 1,000 Da. In some embodiments, the small molecule has a molecular weight of less than 750 Da.

In some embodiments, the small molecule is an aliphatic or aromatic hydrocarbon, either of which optionally can include, either in the linear chain connecting the oligonucleotides or appended to it, one or more functional groups including, but not limited to, hydroxy, amino, thiol, thioether, ether, amide, thioamide, ester, urea, or thiourea. The small molecule can be cyclic or acyclic. Examples of small molecule linkers include, but are not limited to, amino acids, carbohydrates, cyclodextrins, adamantane, cholesterol, haptens, and antibiotics. However, for purposes of describing the non-nucleotide linker, the term "small molecule" is not intended to include a nucleoside.

In some embodiments, the non-nucleotide linker is an alkyl linker or amino linker. The alkyl linker may be branched or unbranched, cyclic or acyclic, substituted or unsubstituted, saturated or unsaturated, chiral, achiral or racemic mixture. The alkyl linkers can have from about 2 to about 18 carbon atoms. In some embodiments such alkyl linkers have from about 2 to about 9 carbon atoms. In other embodiments, the alkyl linker has less than 3 carbon atoms. In further embodiments, the alkyl linker has at least 3 carbon atoms and preferentially more than three carbon atoms. Some alkyl linkers include one or more functional groups including, but not limited to, hydroxy, amino, thiol, thioether, ether, amide, thioamide, ester, urea, and thioether. Such alkyl linkers can include, but are not limited to, 1,2 propanediol, 1,2,3 propanetriol, 1,3 propanediol, 1,2,4-Butanetriol, 1,3,5-Pentanetriol, 3-trimethylamino-1,2-propanediol, Bis-1,5-O-(3'thymidyl(-1,3,5-pentanetriol, Bis-1,5-O-[3'-(1,2-dideoxy-D-robosyl)]-1,3,5-pentanetriol, 3-(2-Hydroxyethyl)-1,5-pentanediol, triethylene glycol hexaethylene glycol, polyethylene glycollinkers (e.g. [- O- CH2-CH2-]$_n$ (n=1-9)), methyl linkers, ethyl linkers, propyl linkers, butyl linkers or hexyl linkers. In some embodiments, such alkyl linkers may include peptides or amino acids.

In some embodiments, the non-nucleotide linker may include, but are not limited to, those listed in Table 3.

TABLE 3

Representative Non-Nucleotidic Linkers

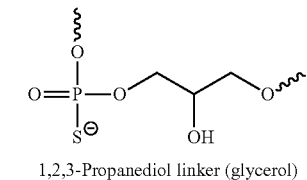

1,2,3-Propanediol linker (glycerol)

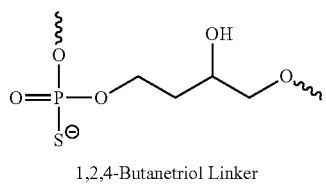

1,2,4-Butanetriol Linker

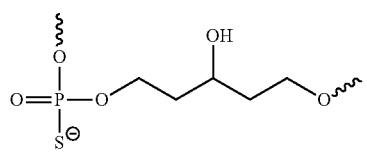

1,3,5-Pentanetriol Linker

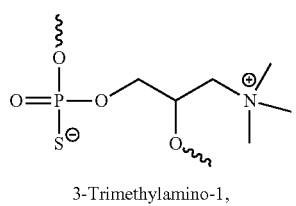

3-Trimethylamino-1,
2-propanediol Linker

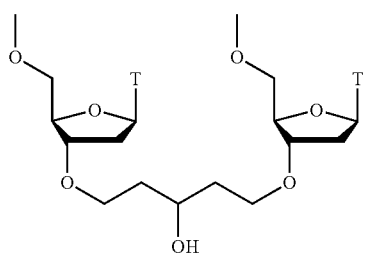

Bis-1,5-O-(3'-thymidyl)-1,3,5-
pentanetriol Linker

TABLE 3-continued

Representative Non-Nucleotidic Linkers

Bis-1,5-O-[3'-(1,2-dideoxy-D-ribosyl)]-1,3-5-pentanetriol Linker 3-(2-Hydroxyethyl)-1,5-pentanediol Linker In some embodiments, the small molecule linker is glycerol or a glycerol homolog of the formula HO—(CH$_2$)$_o$—CH(OH)—(CH$_2$)$_p$—OH, wherein o and p independently are integers from 1 to about 6, from 1 to about 4, or from 1 to about 3. In some other embodiments, the small molecule linker is a derivative of 1,3-diamino-2-hydroxypropane. Some such derivatives have the formula HO—(CH$_2$)$_m$—C(O)NH—CH$_2$—CH(OH)—CH$_2$—NHC(O)—(CH$_2$)$_m$—OH, wherein m is an integer from 0 to about 10, from 0 to about 6, from 2 to about 6, or from 2 to about 4

Some non-nucleotide linkers according to the invention permit attachment of more than two oligonucleotides. For example, the small molecule linker glycerol has three hydroxyl groups to which oligonucleotides may be covalently attached. Some IROs according to the invention, therefore, comprise two or more oligonucleotides linked to a nucleotide or a non-nucleotide linker. Such IROs are referred to as being "branched".

IRO compounds also may comprise at least two oligonucleotides non-covalently linked, such as by electrostatic interactions, hydrophobic interactions, it-stacking interactions, hydrogen bonding and combinations thereof. Non-limiting examples of such non-covalent linkage includes Watson-Crick base pairing, Hoogsteen base pairing and base stacking In preferred embodiments one of the oligonucleotides of the IRO compound is not an antisense oligonucleotide. In more preferred embodiments neither of the oligonucleotides of the IRO compound is an antisense oligonucleotide.

In certain embodiments, pyrimidine nucleosides in the immune regulatory oligonucleotides used in the compositions and methods according to the invention have the structure (II):

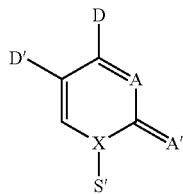

(II)

wherein:
D is a hydrogen bond donor;
D' is selected from the group consisting of hydrogen, hydrogen bond donor, hydrogen bond acceptor, hydrophilic group, hydrophobic group, electron withdrawing group and electron donating group;
A is a hydrogen bond acceptor or a hydrophilic group;
A' is selected from the group consisting of hydrogen bond acceptor, hydrophilic group, hydrophobic group, electron withdrawing group and electron donating group;
X is carbon or nitrogen; and
S' is a pentose or hexose sugar ring, or a sugar analog.

In certain embodiments, the sugar ring is derivatized with a phosphate moiety, modified phosphate moiety, or other linker moiety suitable for linking the pyrimidine nucleoside to another nucleoside or nucleoside analog.

In some embodiments hydrogen bond donors include, without limitation, —NH—, —NH$_2$, —SH and —OH. Preferred hydrogen bond acceptors include, without limitation, C═O, C═S, and the ring nitrogen atoms of an aromatic heterocycle, e.g., N3 of cytosine.

In some embodiments, structure (II) is a pyrimidine nucleoside derivative. Examples of pyrimidine nucleoside derivatives include, without limitation, 5-hydroxycytosine, 5-hydroxymethylcytosine, N4-alkylcytosine, or N4-ethylcytosine, araC, 5-OH-dC, N3-Me-dC, 2'-O-Me-C, 2'-O-Me-U, 2'-O-Me-T, and 4-thiouracil. Chemical modified derivatives also include, but are not limited to, thymine or uracil analogues. In some embodiments, the sugar moiety S' in (II) is a sugar derivative. Suitable sugar derivatives include, but are not limited to, trehalose or trehalose derivatives, hexose or hexose derivatives, arabinose or arabinose derivatives.

In some embodiments, the purine nucleosides in immune regulatory oligonucleotides used in the compositions and methods according to the invention have the structure (III):

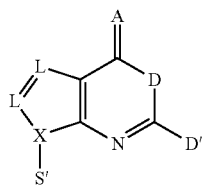

(III)

wherein:
D is a hydrogen bond donor;
D' is selected from the group consisting of hydrogen, hydrogen bond donor, and hydrophilic group;
A is a hydrogen bond acceptor or a hydrophilic group;
X is carbon or nitrogen;
each L is independently selected from the group consisting of C, O, N and S; and
S' is a pentose or hexose sugar ring, or a sugar analog.

In certain embodiments, the sugar ring is derivatized with a phosphate moiety, modified phosphate moiety, or other linker moiety suitable for linking the pyrimidine nucleoside to another nucleoside or nucleoside analog.

In certain embodiments hydrogen bond donors include, without limitation, —NH—, —NH$_2$, —SH and —OH. In certain embodiments hydrogen bond acceptors include, without limitation, C=O, C=S, —NO$_2$ and the ring nitrogen atoms of an aromatic heterocycle, e.g., N1 of guanine In some embodiments, structure (III) is a purine nucleoside derivative. Examples of purine nucleoside derivatives include, without limitation, guanine analogues such as 7-deaza-G, 7-deaza-dG, ara-G, 6-thio-G, Inosine, Iso-G, loxoribine, TOG(7-thio-8-oxo)-G, 8-bromo-G, 8-hydroxy-G, 5-aminoformycin B, Oxoformycin, 7-methyl-G, 9-p-chlorophenyl-8-aza-G, 9-phenyl-G, 9-hexyl-guanine, 7-deaza-9-benzyl-G, 6-Chloro-7-deazaguanine, 6-methoxy-7-deazaguanine, 8-Aza-7-deaza-G(PPG), 2-(Dimethylamino) guanosine, 7-Methyl-6-thioguanosine, 8-Benzyloxyguanosine, 9-Deazaguanosine, 1-(B-D-ribofuranosyl)-2-oxo-7-deaza-8-methyl-purine, 1-(2'-deoxy-β-D-ribofuranosyl)-2-oxo-7-deaza-8-methyl-purine, 2'-O-methyl-G, and N1-Me-dG. Chemically modified derivatives also include, but are not limited to, adenine analogues such as 9-benzyl-8-hydroxy-2-(2-methoxyethoxy)adenine, 2-Amino-N2-O-methyladenosine, 8-Aza-7-deaza-A, 7-deaza-A, Vidarabine, 2-Aminoadenosine, N1-Methyladenosine, 8-Azaadenosine, 5-Iodotubercidin, and2'-O-Me-A. In some embodiments, the sugar moiety S' in (III) is a sugar derivative as defined for Formula II.

In certain embodiments of the invention, the immune regulatory nucleic acid comprises a nucleic acid sequence containing at least one B-L-deoxy nucleoside or 3'-deoxy nucleoside.

In certain embodiments of the invention, the immune regulatory oligonucleotide comprises a nucleic acid sequence containing at least one dinucleotide selected from CpG, C*pG, C*pG* and CpG*, wherein C is cytosine or 2'-deoxycytidine, G is guanosine or 2'-deoxyguanosine, C* is 2'-deoxythymidine, 1-(2'-deoxy-β-D-ribofuranosyl)-2-oxo-7-deaza-8-methyl-purine, 5-Me-dC, 2'-dideoxy-5-halocytosine, 2'-dideoxy-5-nitrocytosine, arabinocytidine, 2'-deoxy-2'-substituted arabinocytidine, 2'-O-substituted arabinocytidine, 2'-deoxy-5-hydroxycytidine, 2'-deoxy-N4-alkyl-cytidine, 2'-deoxy-4-thiouridine, 2'-O-substituted ribonucleotides (including, but not limited to, 2'-O-Me-5-Me-C, 2'-O-(2-methoxyethyl)-ribonucelotides or 2'-O-Me-ribonucleotides) or other pyrimidine nucleoside analogs or derivative, G* is 2'-deoxy-7-deazaguanosine, 2'-deoxy-6-thioguanosine, arabinoguanosine, 2'-deoxy-2'substituted-arabinoguanosine, 2'-O-substituted-arabinoguanosine, 2'-deoxyinosine, 2'-O-substituted ribonucleotides (including, but not limited to, 2'-O-(2-methoxyethyl)-ribonucelotides; or 2'-O-Me-ribonucleotides) or other purine nucleoside analogs or derivative, and p is an internucleoside linkage selected from the group consisting of phosphodiester, phosphorothioate, and phosphorodithioate, and wherein the activity of the at least one dinucleotide is regulated by the flanking sequence.

In some embodiments, the oligonucleotides of the IRO compound each have from about 6 to about 35 nucleoside residues, preferably from about 9 to about 30 nucleoside residues, more preferably from about 11 to about 23 nucleoside residues. In some embodiments, the oligonucleotides have from about 6 to about 18 nucleotide residues.

In some embodiments, the IRO compounds can be combined with one or more vaccines, antigens, antibodies, cytotoxic agents, allergens, antibiotics, antisense oligonucleotides, TLR agonist, TLR antagonist, peptides, proteins, gene therapy vectors, DNA vaccines, adjuvants or kinase inhibitors to enhance the specificity or magnitude of the immune response, or co-stimulatory molecules such as cytokines, chemokines, protein ligands, trans-activating factors, peptides and peptides comprising modified amino acids.

In a second aspect, the invention provides a pharmaceutical composition comprising an IRO compound according to the invention and a physiologically acceptable carrier.

In embodiments of this aspect of the invention, the composition can further comprise one or more vaccines, antigens, antibodies, cytotoxic agents, allergens, antibiotics, antisense oligonucleotides, TLR agonist, TLR antagonist, peptides, proteins, gene therapy vectors, DNA vaccines, adjuvants or kinase inhibitors to enhance the specificity or magnitude of the immune response, or co-stimulatory molecules such as cytokines, chemokines, protein ligands, trans-activating factors, peptides and peptides comprising modified amino acids.

In a third aspect, the invention provides methods for inhibiting or suppressing TLR-mediated induction of an immune response in a mammal, such methods comprising administering to the mammal an IRO compound according to the invention. In some embodiments, the mammal is a human. In preferred embodiments, the IRO compound is administered to a mammal in need of immune suppression.

According to this aspect of the invention, an IRO compound is capable of suppressing a TLR-based immune response to a further TLR ligand or TLR agonist. As discussed further in the Examples below, the activation of a TLR-based immune response by a TLR agonist or TLR ligand (for example, an immune stimulatory oligonucleotide) can be antagonized, inhibited, suppressed or prevented by the simultaneous, pre- or post-administration of an IRO compound, and such antagonism, inhibition, suppression or prevention may be maintained for an extended period of time (for example, days) after administration. This beneficial property of the current invention has a unique advantage for the prevention and/or treatment of a disease or disorder. For example, application of certain TLR-agonists in the course of treating the disease may cause unwanted immune stimulation that an IRO compound could antagonize, suppress, inhibit or prevent. Administration of the IRO simultaneously, pre and/or post administration of the TLR-agonist may allow therapeutic benefits from the TLR-agonist while antagonizing, suppressing, inhibiting or preventing the unwanted side effect(s). Additionally, pre-administration of an IRO compound according to the invention could antagonize, suppress, inhibit or prevent an immune response (for example, an allergic reaction) to a subsequent or later challenge by a TLR-agonist. Preferably a TLR7 and/or TLR9 agonist In the methods according to this aspect of the invention, administration of IRO compound according to the invention can be by any suitable route, including, without limitation, parenteral, mucosal delivery, oral, sublingual, transdermal, topical, inhalation, intragastric, intranasal, aerosol, intraocular, intratracheal, intrarectal, vaginal, by gene gun, dermal patch or in eye drop or mouthwash form. Administration of the therapeutic compositions of IRO compound can be carried out using known procedures at dosages and for periods of time effective to reduce symptoms or surrogate markers of the disease. When administered systemically, the therapeutic composition is preferably administered at a sufficient dosage to attain a blood concentration of IRO compound from about 0.0001 micromolar to about 100 micromolar. More preferably, systemic administration would be at a sufficient dosage to attain a blood concentration of the IRO compound from about 0.001 micromolar to about 10 micromolar. For localized administration, much lower concentrations than this may be effective, and much higher concentrations may be tolerated. Preferably, a total dosage of IRO compound ranges from about 0.001 mg per patient per day to about 200 mg per kg body weight per day. It may be desirable to administer the IRO compound according to the invention daily, every second day, every third day, every fourth day, every fifth day, every sixth day or weekly. It may be desirable to administer simultaneously, or sequentially, a therapeutically effective amount of one or more of the IRO containing therapeutic compositions of the invention to an individual as a single treatment episode.

The IRO compound may optionally be linked to one or more allergens and/or antigens (self or foreign), an immunogenic protein, such as keyhole limpet hemocyanin (KLH), cholera toxin B subunit, or any other immunogenic carrier protein. IRO can also be used in combination with other compounds (for example, adjuvants) including, without limitation, TLR agonists (e.g. TLR2 agonists, TLR4 agonists, and TLR9 agonists), Freund's incomplete adjuvant, KLH, monophosphoryl lipid A (MPL), alum, Merck alum adjuvant (MAA), and saponins, including QS-21 and imiquimod, or combinations thereof The methods according to this aspect of the invention are useful for model studies of the immune system. The methods are also useful for the prophylactic or therapeutic treatment of human or animal disease. For example, the methods are useful for pediatric, adult, and veterinary vaccine applications.

In a fourth aspect, the invention provides methods for therapeutically treating a patient having a disease or disorder, such methods comprising administering to the patient a IRO compound according to the invention. In various embodiments, the disease or disorder to be treated is cancer, an autoimmune disorder, airway inflammation, inflammatory disorders, infectious disease, malaria, Lyme disease, ocular infections, conjunctivitis, skin disorders, psoriasis, scleroderma, cardiovascular disease, atherosclerosis, chronic fatigue syndrome, sarcoidosis, transplant rejection, allergy, asthma or a disease caused by a pathogen. Preferred autoimmune disorders include without limitation lupus erythematosus, multiple sclerosis, type I diabetes mellitus, irritable bowel syndrome, Chron's disease, rheumatoid arthritis, septic shock, alopecia universalis, acute disseminated encephalomyelitis, Addison's disease, ankylosing spondylitis, antiphospholipid antibody syndrome, autoimmune hemolytic anemia, autoimmune hepatitis, Bullous pemphigoid, chagas disease, chronic obstructive pulmonary disease, coeliac disease, dermatomyositis, endometriosis, Goodpasture's syndrome, Graves' disease, Guillain-Barré syndrome, Hashimoto's disease, hidradenitis suppurativa, idiopathic thrombocytopenic purpura, interstitial cystitis, morphea, myasthenia gravis, narcolepsy, neuromyotonia, pemphigus, pernicious anaemia, polymyositis, primary biliary cirrhosis, schizophrenia, Sjögren's syndrome, temporal arteritis ("giant cell arteritis"), vasculitis, vitiligo, vulvodynia and Wegener's granulomatosis. Preferred inflammatory disorders include without limitation airway inflammation, asthma, autoimmune diseases, chronic inflammation, chronic prostatitis, glomerulonephritis, Behçet's disease, hypersensitivities, inflammatory bowel disease, reperfusion injury, rheumatoid arthritis, transplant rejection, ulcerative colitis, uveitis, conjunctivitis and vasculitis. Pathogens include bacteria, parasites, fungi, viruses, viroids, and prions. Administration is carried out as described for the third aspect of the invention.

In a fifth aspect, the invention provides methods for preventing a disease or disorder, such methods comprising administering to the patient IRO compound according to the invention. In various embodiments, the disease or disorder to be prevented is cancer, an autoimmune disorder, airway inflammation, inflammatory disorders, infectious disease, malaria, Lyme disease, ocular infections, conjunctivitis, skin disorders, psoriasis, scleroderma, cardiovascular disease, atherosclerosis, chronic fatigue syndrome, sarcoidosis, transplant rejection, allergy, asthma or a disease caused by a pathogen. Preferred autoimmune disorders include without limitation lupus erythematosus, multiple sclerosis, type I diabetes mellitus, irritable bowel syndrome, Chron's disease, rheumatoid arthritis, septic shock, alopecia universalis, acute disseminated encephalomyelitis, Addison's disease, ankylosing spondylitis, antiphospholipid antibody syndrome, autoimmune hemolytic anemia, autoimmune hepatitis, Bullous pemphigoid, chagas disease, chronic obstructive pulmonary disease, coeliac disease, dermatomyositis, endometriosis, Goodpasture's syndrome, Graves' disease, Guillain-Barré syndrome, Hashimoto's disease, hidradenitis suppurativa, idiopathic thrombocytopenic purpura, interstitial cystitis, morphea, myasthenia gravis, narcolepsy, neuromyotonia, pemphigus, pernicious anaemia, polymyositis, primary biliary cirrhosis, schizophrenia, Sjögren's syndrome, temporal arteritis ("giant cell arteritis"), vasculitis, vitiligo, vulvodynia and Wegener's granulomatosis. Preferred inflammatory disorders include without limitation airway inflammation, asthma, autoimmune diseases, chronic inflammation, chronic prostatitis, glomerulonephritis, Behçet's disease, hypersensitivities, inflammatory bowel disease, reperfusion injury, rheumatoid arthritis, transplant rejection, ulcerative colitis, uveitis, conjunctivitis and vasculitis. Pathogens include bacteria, parasites, fungi, viruses, viroids, and prions. Administration is carried out as described for the third aspect of the invention.

In any of the methods according to the third, fourth or fifth aspect of the invention, the IRO compound can be administered in combination with any other agent useful for treating or preventing the disease or condition that does not abolish the immune antagonist, inhibitory, suppression or prevention effect or activity of the IRO compound. In any of the methods according to the invention, the agent useful for treating or preventing the disease or condition includes, but is not limited to, one or more vaccines, antigens, antibodies, cytotoxic agents, allergens, antibiotics, antisense oligonucleotides, TLR agonist, TLR antagonist, peptides, proteins, gene therapy vectors, DNA vaccines, adjuvants or kinase inhibitors to enhance the specificity or magnitude of the immune response, or co-stimulatory molecules such as cytokines, chemokines, protein ligands, trans-activating factors, peptides and peptides comprising modified amino acids. For example, in the treatment of cancer, it is contemplated that the IRO compound may be administered in combination with one or more chemotherapeutic compound, targeted therapeutic agent and/or monoclonal antibody; And in preventing a disease, it is contemplated that the IRO compound may be administered in combination with one or more vaccine. Alternatively, the agent can include DNA vectors encoding for antigen or allergen. In these embodiments, the IRO compounds of the invention can variously act as adjuvants and/or produce direct immune modulatory effects.

The following examples are intended to further illustrate certain exemplary embodiments of the invention and are not intended to limit the scope of the invention. For example, representative TLR-ligands are shown in the following examples, but do not limit the scope of ligands to which the IROs of the invention act as antagonists.

Example 1

Synthesis of Oligonucleotides Containing Immune Regulatory Moieties

All IRO compounds of the invention were synthesized according to standard procedures (see e.g. U.S. Patent Publication No. 20040097719).

Oligonucleotides were synthesized on a 1 μM scale using an automated DNA synthesizer (Expedite 8909; PerSeptive Biosystems, Framingham, Mass.), following standard linear synthesis or parallel synthesis procedures (see e.g. FIGS. 5 and 6 of U.S. Patent Publication No. 20040097719).

Deoxyribonucleoside phosphoramidites were obtained from (Aldrich-Sigma, St Louis, Mo.). 1',2'-dideoxyribose phosphoramidite, propyl-1-phosphoramidite, 2-deoxyuridine phosphoramidite, 1,3-bis-[5-(4,4'-dimethoxytrityl)pentylamidyl]-2-propanolphosphoramidite and methyl phosponamidite were obtained from Glen Research (Sterling, Va.). .beta.-L-2'-deoxyribonucleoside phosphoramidite, .alpha.-2'-deoxyribonucleoside phosphoramidite, mono-DMT-glycerol phosphoramidite and di-DMT-glycerol phosphoramidite were obtained from ChemGenes (Willmington, Mass.). (4-Aminobutyl)-1,3-propanediol phosphoramidite was obtained from Clontech (Palo Alto, Calif.). Arabinoguanosine, was obtained from Reliable Pharmaceutical (St. Louis, Mo.). Arabinoguanosine phosphoramidite was synthesized at Idera Pharmaceuticals, Inc. (Cambridge, Mass.) (Noronha et al. (2000) Biochem., 39:7050-7062).

All nucleoside phosphoramidites were characterized by $^{31}$P and $^{1}$H NMR spectra. Modified nucleosides were incorporated at specific sites using normal coupling cycles. After synthesis, oligonucleotides were deprotected using concentrated ammonium hydroxide and purified by reverse phase HPLC, followed by dialysis. Purified oligonucleotides as sodium salt form were lyophilized prior to use. Purity was tested by CGE and MALDI-TOF MS.

Example 2

Inhibition of TLR7 and TLR9 Stimulation

C57BL/6 mice were injected s.c. at left underarm with 5 mg/kg of an IRO compound at 0 hours and 0.25 mg/kg TLR9 agonist or 10 mg/kg TLR7 agonist at 24 hours. Serum samples were taken at 2 hours after injection of the TLR9 or TLR7 agonist and IL-12 concentration was determined by ELISA. For IRO number 40, the TLR7 and TLR9 agonists were administered 72 hours after administration of the IRO. The results for all IROs are shown in Tables 4-11. These results demonstrate that an IRO compound according to the invention can inhibit TLR7 and/or TLR9 activity in vivo, and more generally that IRO compounds according to the invention can inhibit TLR activation.

TABLE 4

Antagonist Activity in vivo in mice

| Oligo No. | Sequences and Modification | % Inhibition of TLR9 agonist induced IL-12 | % Inhibition of TLR7 agonist induced IL-12 |
|---|---|---|---|
| 1 | 5'-UGUCG1TTCT-X1-TCTTG1CUGU-5' | 44.8 | 94.0 |
| 2 | 5'-UGUCG1TTC-X1-CTTG1CUGU-5' | 69.8 | 91.6 |
| 3 | 5'-UGUCG1TT-X1-TTG1CUGU-5' | 63.7 | 89.8 |
| 4 | 5'-UGUCoG1TTCTo-Z-oTCTTG1oCUGU-5' | 27.6 | 53.7 |
| 5 | 5'-GUCG1TTCTT-Z-TTCTTG1CUG-5' | 75.9 | 97.1 |
| 6 | 5'-UGUCG2TTCT-Z-TCTTG2CUGU-5' | 70.9 | 99.0 |
| 7 | 5'-UGUCG1TTCT-X4-TCTTG1CUGU-5' | 83.2 | 92.6 |
| 8 | 5'-UGUCG1TTC-X4-CTTG1CUGU-5' | 68.7 | 78.5 |
| 9 | 5'-UGUCoG1TTCTo-X4-oTCTTG1oCUGU-5' | 76.5 | 18.6 |
| 10 | 5'-GUCG1TTCTT-X4-TTCTTG1CUG-5' | 87.8 | 100 |
| 11 | 5'-UGUCG1TT-X4-TTG1CUGU-5' | 31.1 | 56.8 |
| 12 | 5'-UGUCG1TTC-X5-CTTG1CUGU-5' | 7.3 | 80.4 |
| 13 | 5'-UGUCG2TTC-X5-CTTG2CUGU-5' | 48.6 | 98.1 |
| 14 | 5'-UGUCG1TTC-X6-CTTG1CUGU-5' | 64.6 | 92.2 |
| 15 | 5'-UGUCG2TTC-X6-CTTG2CUGU-5' | 57.1 | 99.9 |
| 16 | 5'-UGUCG1TTCT-X7-TCTTG1CUGU-5' | 96.5 | 98.5 |
| 17 | 5'-UGUCG2TTCT-X7-TCTTG2CUGU-5' | 86.2 | 97.3 |
| 18 | 5'-UGUCG1TTC-X7-CTTG1CUGU-5' | 94.0 | 98.1 |

TABLE 5

Antagonist Activity in vivo in mice

| Oligo No. | Sequences and Modification | % Inhibition of TLR9 agonist induced IL-12 | % Inhibition of TLR7 agonist induced IL12 |
|---|---|---|---|
| 19 | 5'-TGUCG1TTCT-X-TCTTG1CUGT-5' | 45.2 | 89.8 |
| 20 | 5'-CTTGUCG1TTCT-X-TCTTG1CUGTTC-5' | 74.5 | 77.9 |
| 21 | 5'-TTGUCG1TTC-X-CTTG1CUGTT-5' | 66.5 | 86.8 |
| 22 | 5'-CTTTGUCG1TTC-X-CTTG1CUGTTTC-5' | 47.5 | 88.9 |
| 23 | 5'-TGUCG1TTCT-X7-TCTTG1CUGT-5' | 45.4 | 83.6 |
| 24 | 5'-TTGUCG1TTC-X7-CTTG1CUGTT-5' | 42.5 | 88.3 |
| 25 | 5'-GUCG1TTCTT-Z-TTCTTG1CUG-5' | 80.4 | 92.3 |
| 26 | 5'-TGUCG1TTCA-X-ACTTG1CUGT-5' | 65.8 | 93.2 |

TABLE 6

Antagonist Activity in vivo in mice

| Oligo No. | Sequences and Modification | % Inhibition of TLR9 agonist induced IL-12 |
|---|---|---|
| 27 | 5'-TCTGACG1TTCT-X-TCTTG1CAGTCT-5' | 95.8 |
| 28 | 5'-TCTGACG2TTCT-X-TCTTG2CAGTCT-5' | 97.4 |

TABLE 7

Antagonist Activity in vivo in mice

| Oligo No. | Sequences and Modification | % Inhibition of TLR9 agonist induced IL-12 | % Inhibition of TLR7 agonist induced IL12 |
|---|---|---|---|
| 29 | 5'-TTGUCG1TTA-X-ATTG1CUGTT-5' | 36.6 | 95.3 |
| 30 | 5'-CTCTGUCG1TTA-X-ATTG1CUGTCTC-5' | 22.6 | 91.6 |
| 31 | 5'-TGTC*GTTCT-X-TCTTGC*TGT-5' | 78.9 | |
| 32 | 5'-TGTCGTTCT-X-TCTTGCTGT-5' | 73.4 | |
| 33 | 5'-TGTC*GTTCT-X-TCTTGC*TGT-5' | 75.5 | |
| 34 | 5'-TGTCGTTCT-X-TCTTGCTGT-5' | 85.8 | |

TABLE 8

Antagonist Activity in vivo in mice

| Oligo No. | Sequences and Modification | % Inhibition of TLR9 agonist induced IL-12 |
|---|---|---|
| 35 | 5'-UGUCG1ACAT-X-TACAG1CUGU-5' | 65.1 |
| 36 | 5'-UGUCG1TTC-X-CTTG1CUGU-5' | 35.7 |
| 37 | 5'-UGUCG1TT-X-TTG1CUGU-5' | 26.5 |
| 38 | 5'-UoGUCG1TToCTo-X-oTCoTTG1CUGoU-5' | 6.9 |
| 39 | 5'-UoGoUCG1TTCTo-X-oTCTTG1CUoGoU-5' | 16.8 |

TABLE 9

Antagonist Activity in vivo in mice

| Oligo No. | Sequences and Modification | % Inhibition of TLR9 agonist induced IL-12 |
|---|---|---|
| 40 | 5'-UGACG1TTCT-X-TCTTG1CAGU-5' | 54.9 |

TABLE 10

Antagonist Activity in vivo in mice

| Oligo No. | Sequences and Modification | % Inhibition of TLR9 agonist induced IL-12 |
|---|---|---|
| 41 | 5'-UGUCG1ACAT-Z-TACAG1CUGU-5' | 86.9 |
| 42 | 5'-UGUCG1TTCT-Z-TCTTG1CUGU-5' | 69.6 |
| 43 | 5'-UGUCG1TTC-Z-CTTG1CUGU-5' | 60.8 |
| 44 | 5'-UGUCG1TT-Z-TTG1CUGU-5' | 43.8 |

TABLE 11

Antagonist Activity in vivo in mice

| oligo No. | Sequences and Modification | % Inhibition of TLR9 agonist induced IL-12 | % Inhibition of TLR7 agonist induced IL12 |
|---|---|---|---|
| 58 | 5'-CTATCTGAC*GTTCTCTGT-3' | 72.6 | 79.8 |
| 62 | 5'-CTATCTG^A^CGTTCTCTGT-3' | 68.1 | 30.9 |

TABLE 12

Antagonist Activity in vivo in mice

| oligo No. | Sequence | % Inhibition of IL-12 TLR9 | % Inhibition of IL-12 TLR7 |
|---|---|---|---|
| 71 | 5'-CTTTGUC*G1TTC-X-CTTG1C*UGTTTC-5' | 55.5 | 94.9 |
| 77 | 5'-CTTGUC*G1TTCT-X-TCTTG1C*UGTTC-5' | 71.5 | 92.8 |
| 78 | 5'-CTTTGUC*oG1TTC-X-CTTG1oC*UGTTTC-5' | 25.6 | 83.4 |
| 80 | 5'-CTTGUC*oG1TTCT-X-TCTTG1oC*UGTTC-5' | 6.7 | 68.2 |
| 82 | 5'-CTGUC*oG1TTCTT-X-TTCTTG1oC*UGTC-5' | 9.0 | 78.4 |
| 88 | 5'-CTATCTGUC*G1TTCTCTGT-3' | 63.2 | 77.7 |
| 89 | 5'-CTATCTGUC*G1TTCTCTGT-3' | 36.4 | 40.5 |

Example 3

TLR7/TLR9 in vitro Antagonist Study

Figure 3:
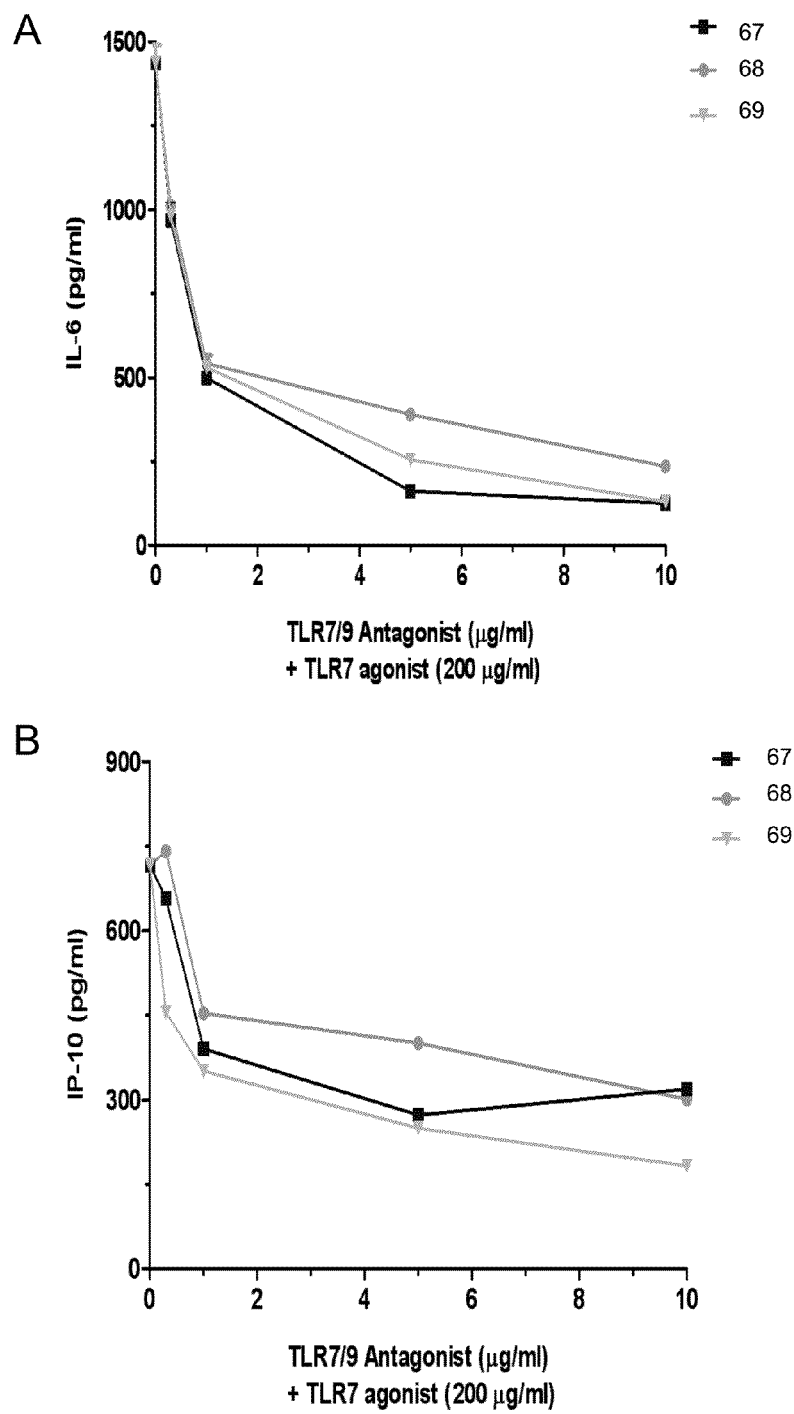
FIGS. 3A-3C depict the ability of TLR7/9 antagonists according to the invention to inhibit TLR7-induced cytokines/chemokines by TLR7/9 antagonists in mouse splenocytes treated according to Example 3.
Figure 3:
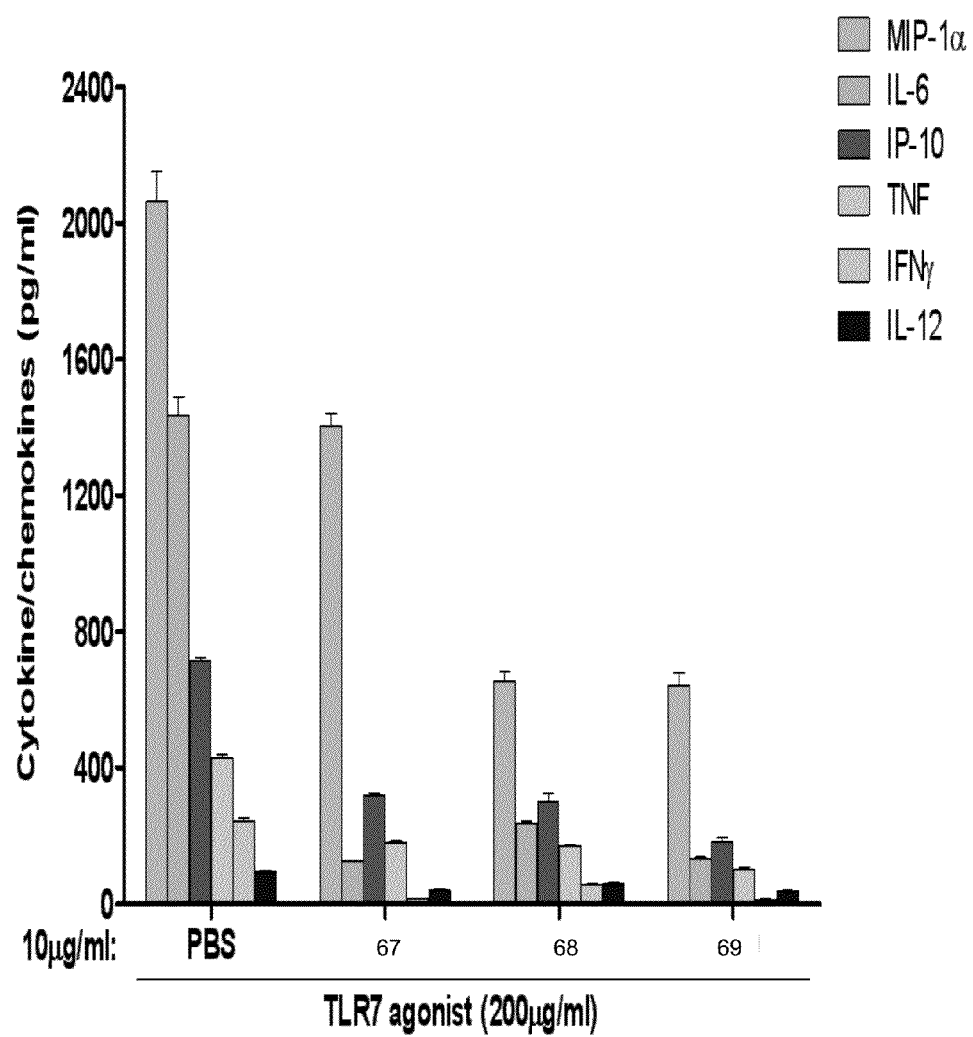
Figure 4:
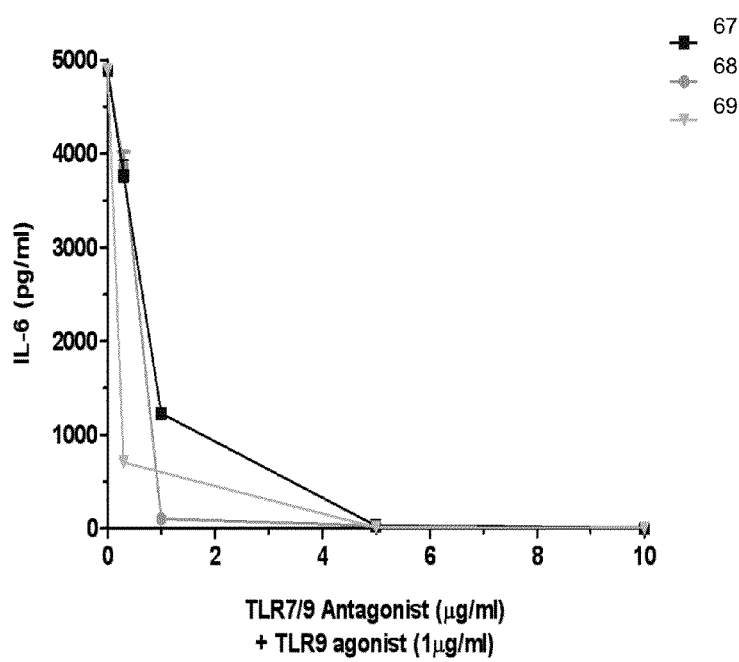
FIGS. 4A-4C depict the ability of TLR7/9 antagonists according to the invention to inhibit TLR9-induced cytokines/chemokines by TLR7/9 antagonists in mouse splenocytes treated according to Example 3.
Figure 4:
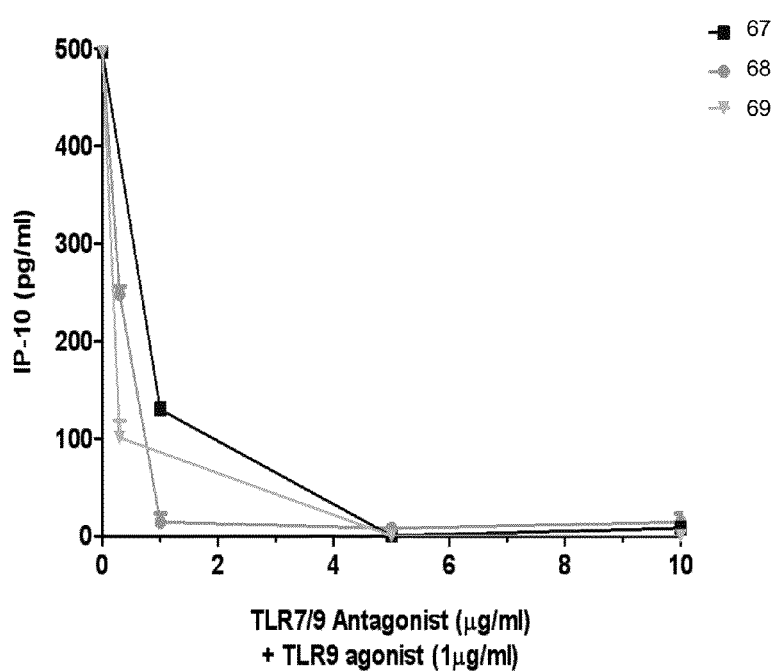
Figure 4:
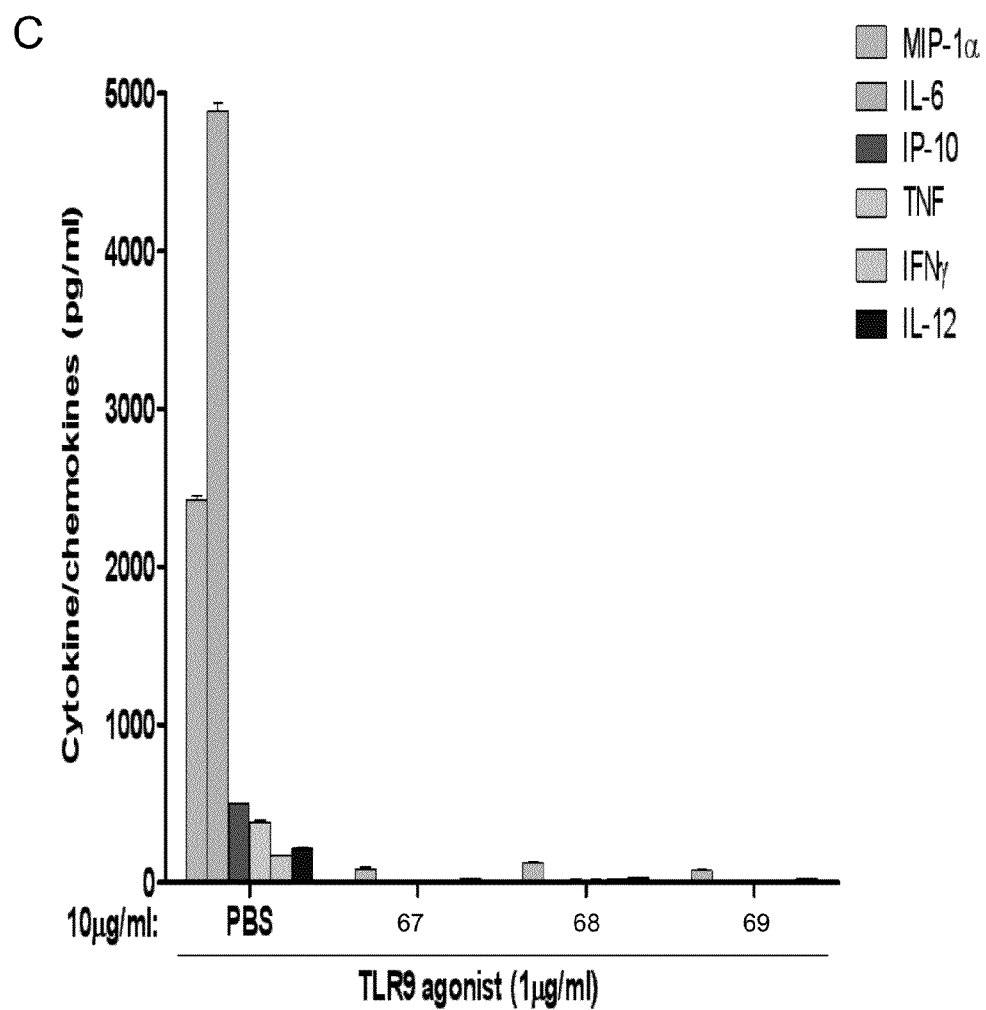

C57BL/6 mice were used in this study. Mouse splenocytes were cultured for 24 hrs (at 37° C., 5% CO$_2$) with TLR7/TLR9 antagonists over a dose range 0.3, 1, 5, 10 mg/ml or at a single dose, 10 mg/ml in the presence of a TLR7 agonist (200 mg/ml) or in the presence of a TLR9 agonist (1 mg/ml) or in the presence of PBS. Supernatants were collected and cytokine/chemokine responses were then evaluated in supernatants by multiplex assays using the Luminex xMAP system. Samples were assayed in duplicate (±SD). Results are shown in FIGS. 3 and 4.

Example 4

TLR7/TLR9 in vivo Antagonist Study

Figure 5:
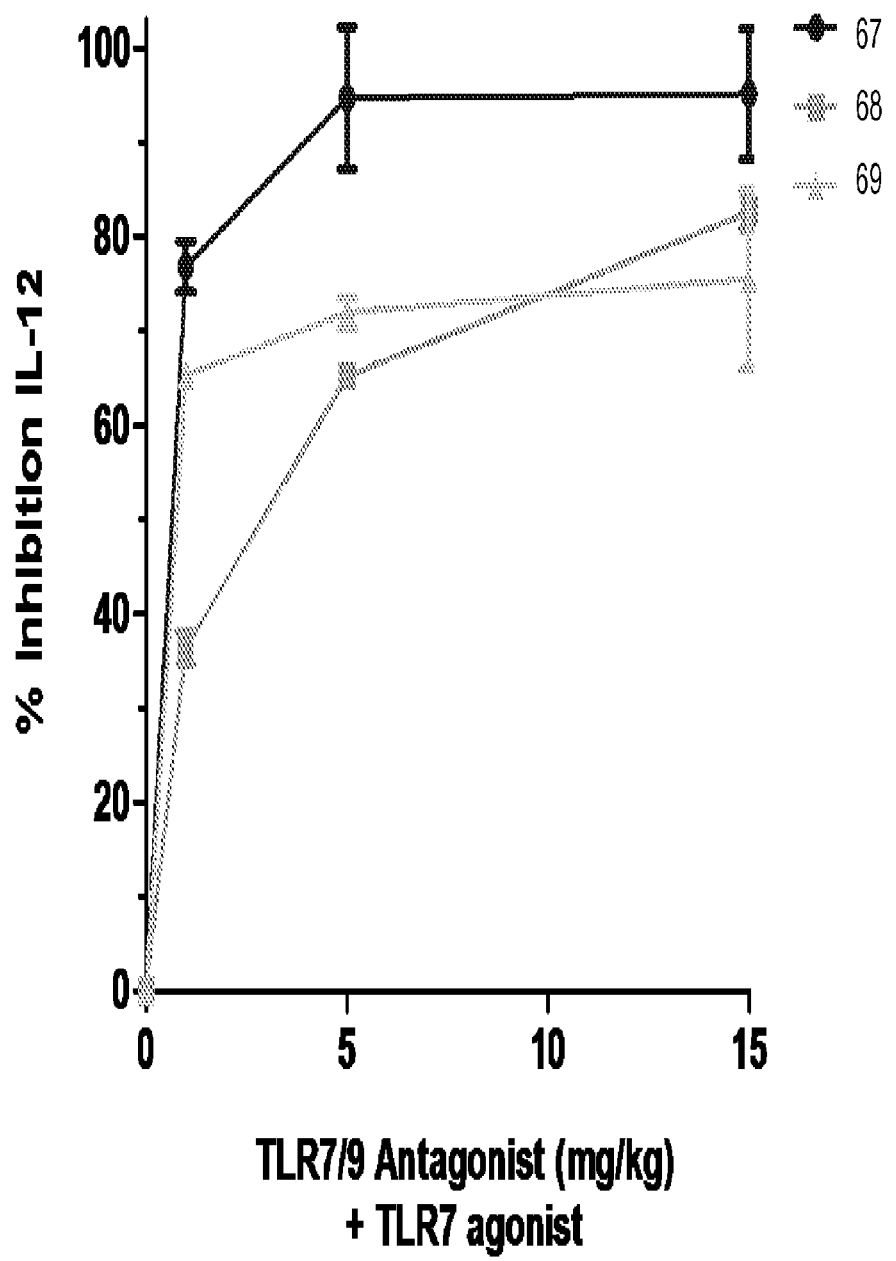
FIG. 5 depicts the ability of TLR7/9 antagonists according to the invention to inhibit TLR7-induced IL-12 in vivo in mice treated according to Example 4.
Figure 6:
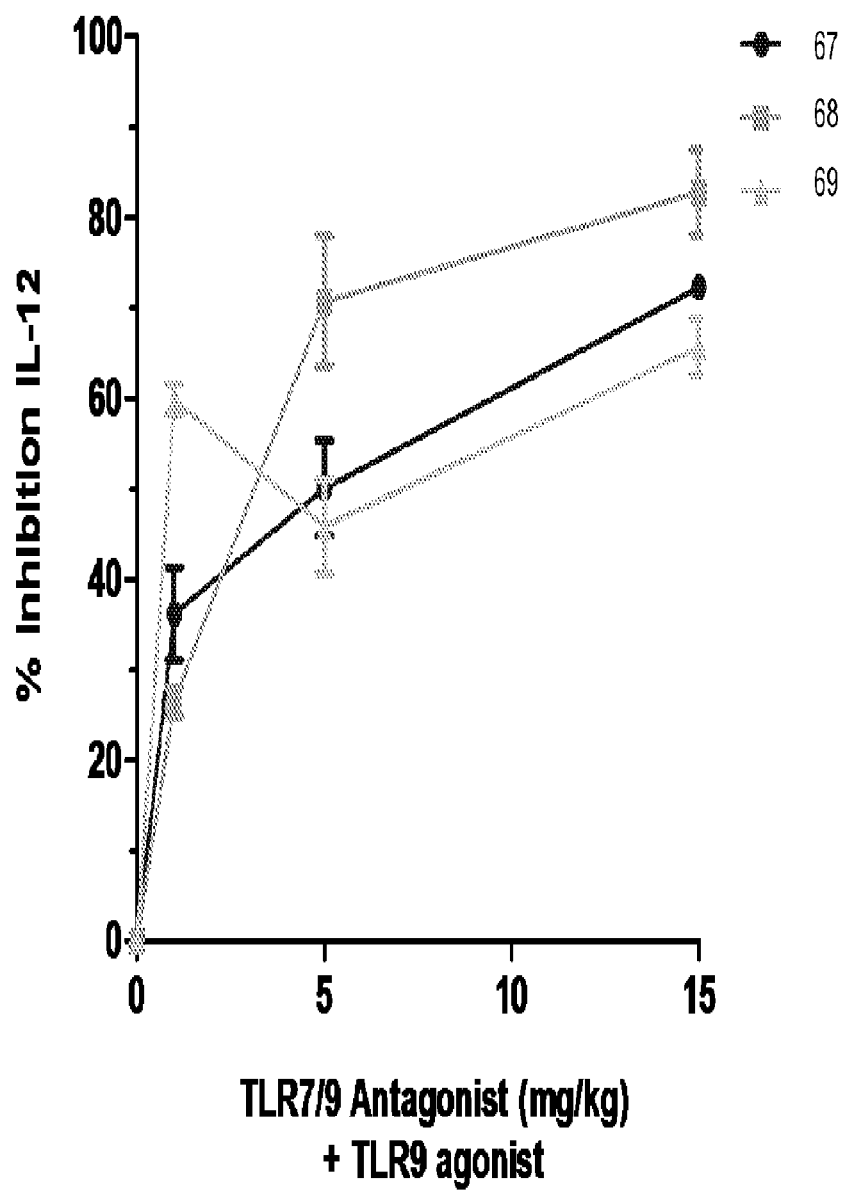
FIG. 6 depicts the ability of TLR7/9 antagonists according to the invention to inhibit TLR9-induced IL-12 in vivo in mice treated according to Example 4.

Female C57BL/6 mice (2/group) were s.c injected with 1, 5 or 15 mg/kg antagonist compound at 0 hr in the right flank. The mice were then injected with TLR7 agonist (10 mg/kg) or with TLR9 agonist (0.25 mg/kg) at 24 hrs in the left flank. Blood was collected by orbital bleeding 2 hrs post the agonist administration. The serum samples were then analyzed by IL-12 ELISA. Results are shown in FIGS. 5 and 6.

Figure 7:
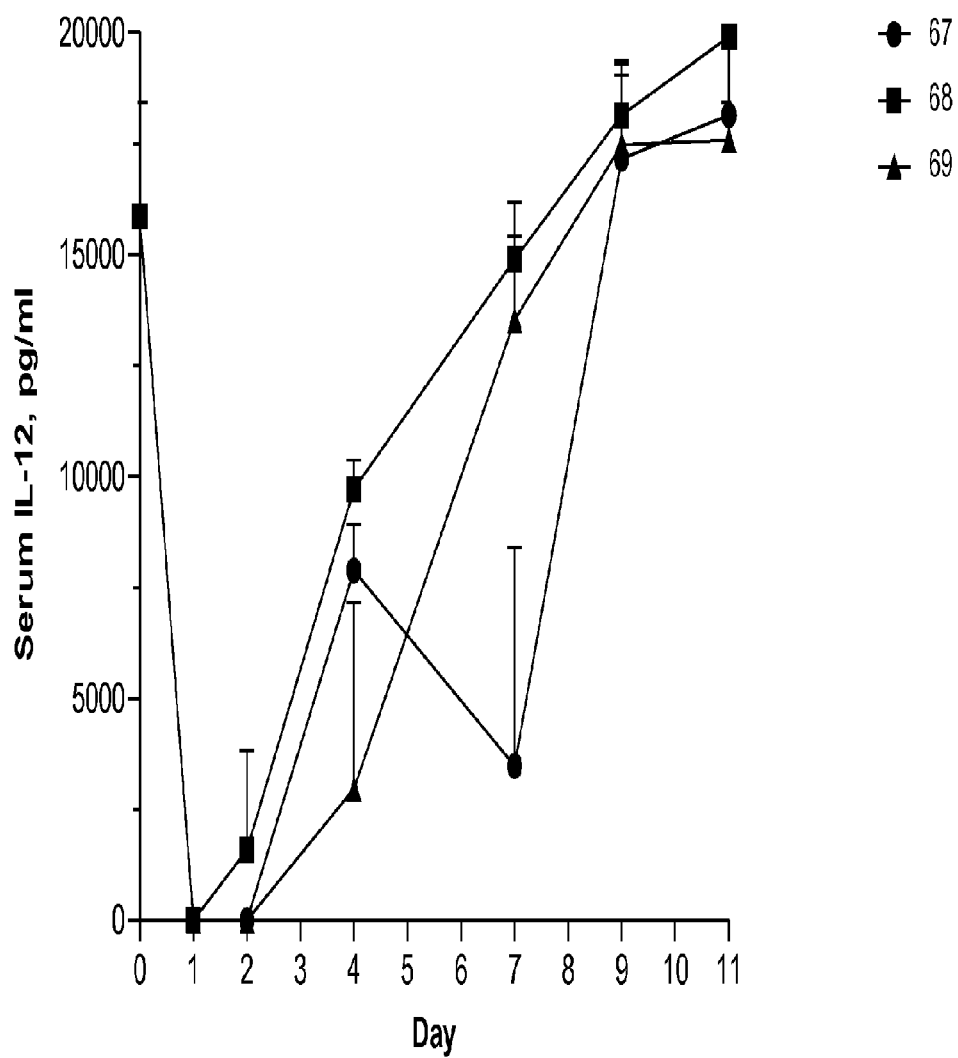
FIG. 7 depicts the ability of TLR7/9 antagonists according to the invention to inhibit TLR7-induced IL-12 in vivo over time in mice treated according to Example 4.
Figure 8:
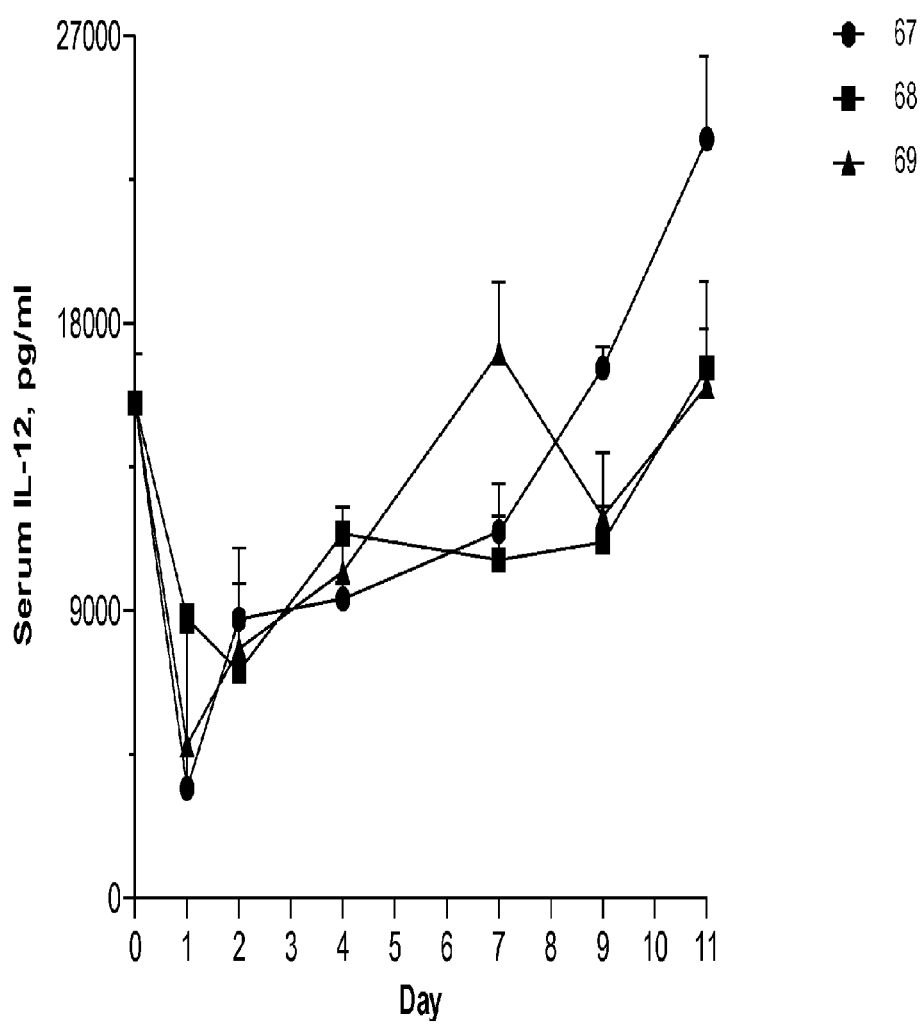
FIG. 8 depicts the ability of TLR7/9 antagonists according to the invention to inhibit TLR9-induced inhibition of IL-12 in vivo over time in mice treated according to Example 4.

Additionally, female C57BL/6 mice (2/group) were s.c injected with 5 mg/kg antagonist compound at day 0 in the right flank. The mice were then injected with TLR7 (10 mg/kg) agonist at days 1, 2, 4, 9 and 11 or with TLR9 (0.25 mg/kg) agonist at days 1, 2, 4, 7, 9 and 11 in the left flank. Blood was collected by orbital bleeding 2 hrs post the agonist administration. The serum samples were then analyzed by IL-12 ELISA. Results are shown in FIGS. 7 and 8.

Figure 9:
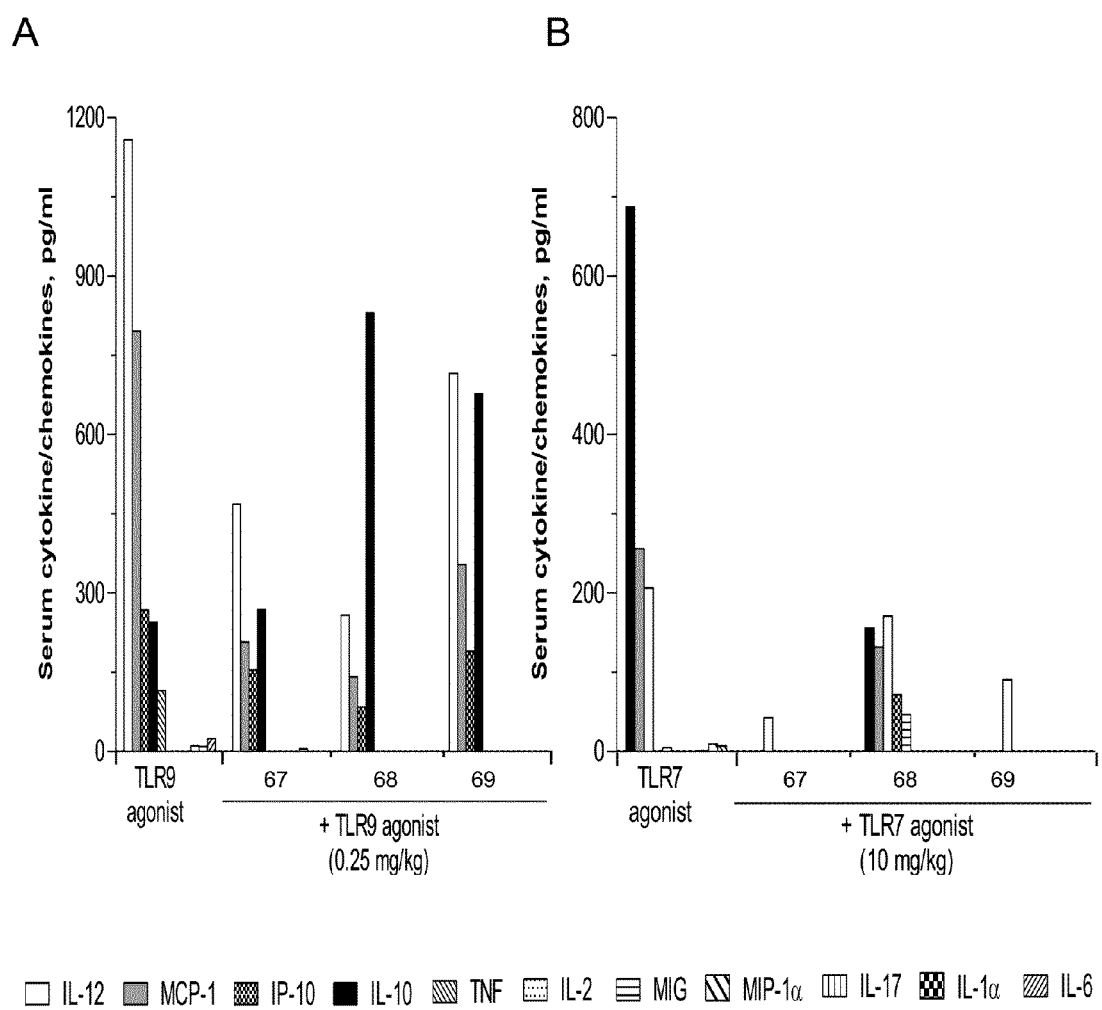
FIGS. 9A-9B depict the ability of TLR7/9 antagonists according to the invention to selectively inhibit mouse TLR7 & 9-induced cytokines in vivo in mice treated according to Example 4.

Female C57BL/6 mice (2/group) were also s.c injected with 5 mg/kg antagonist compound at 0 hr in the right flank. The mice were then injected with TLR9 (0.25 mg/kg) or TLR7 (10 mg/kg) agonists at 24 hrs in the left flank. Blood was collected by orbital bleeding 2 hrs post the agonist administration. Cytokine/chemokine responses were then evaluated in serum samples by multiplex assays using the Luminex xMAP system. Results are shown in FIG. 9.

Figure 10:
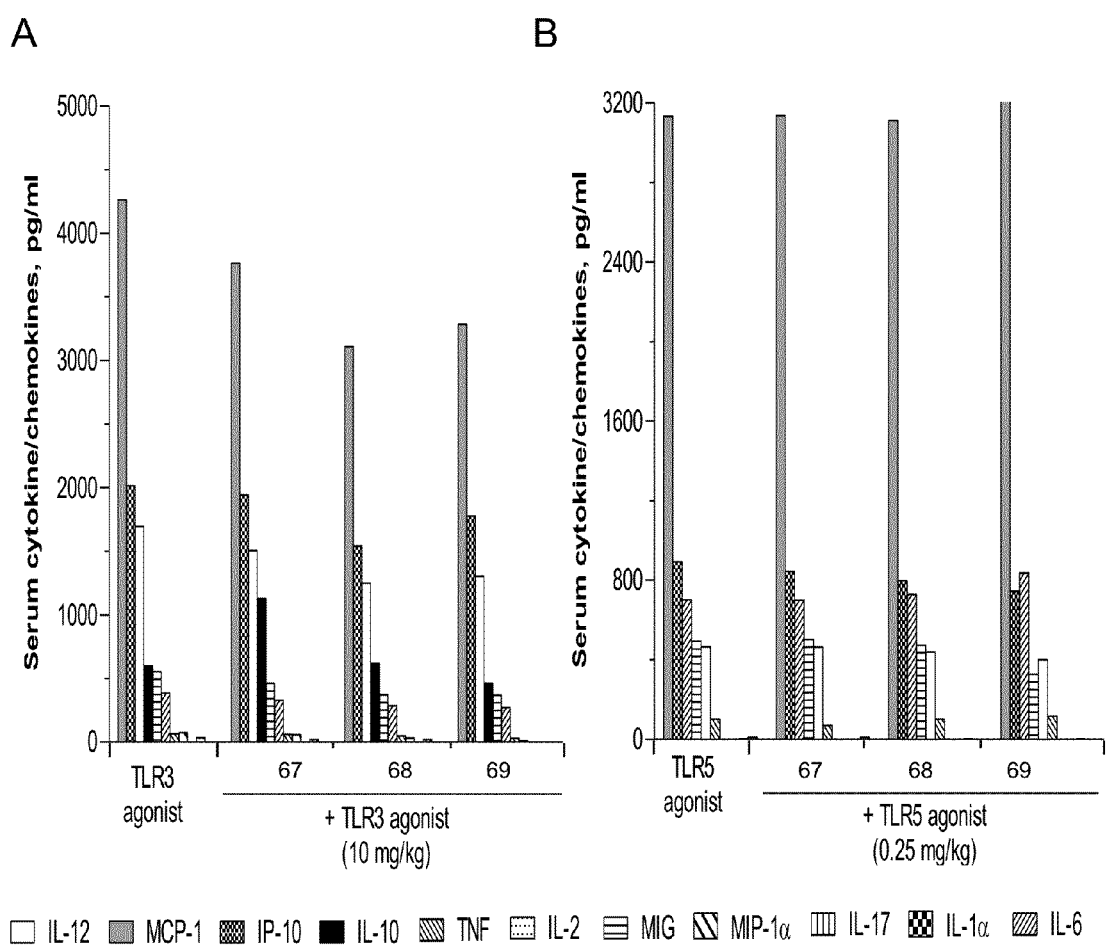
FIGS. 10A-10B demonstrate that TLR 7/9 antagonists according to the invention do not inhibit the activity of TLR3 or TLR5 in vivo in mice treated according to Example 4.

Finally, female C57BL/6 mice (2/group) were s.c injected with 5 mg/kg antagonist compound at 0 hr in the right flank. The mice were then injected with TLR3 (10 mg/kg) or TLR5 (0.25 mg/kg) agonists at 24 hrs in the left flank. Blood was collected by orbital bleeding 2 hrs post the agonist administration. Cytokine/chemokine responses were then evaluated in serum samples by multiplex assays using the Luminex xMAP system. Results are shown in FIG. 10.

The invention claimed is:

1. A method for therapeutically treating a mammal having cancer where inhibiting a TLR7- and/or TLR9-mediated immune response would be beneficial, such method comprising administering to the mammal an antagonist of TLR7 and/or TLR9 having the structure 5'—$N_pN_3N_2N_1$C*G1$N^1N^2N^3N^-N^4N^5$-3' (SEQ ID NO: 72), wherein
C*G* is an oligonucleotide motif wherein C* is 5-Me-dC, and G1 is 7-deaza-dG;
$N_1$—$N_2$, at each occurrence, is independently a 2'-O-Me-ribonucleotide;
$N^3$, at each occurrence, is independently a nucleotide;
$N^1$—$N^3$, at each occurrence, is independently a nucleotide;
$N_m$ and $N^m$, at each occurrence, is independently a nucleotide;
$N^4$—$N^5$, at each occurrence, is independently a 2'-O-Me-ribonucleotide;

p is 5; and
z is 3;
provided that the compound contains less than 3 consecutive guanosines.

2. The method according to claim 1, wherein the antagonist has the structure 5'-CTATCTG<u>U</u>C*G1TTCTCTG<u>U</u>-3' (SEQ ID NO: 42) or 5'-CTATCTG<u>A</u>C*G1TTCTCTG<u>U</u>-3' (SEQ ID NO: 68), wherein <u>G</u>, <u>A</u>, or <u>U</u>=2-O-e-ribonucleotide, C*=5-Me-dC, and G1 =7-deaza-dG.

3. The method according to claim 1, wherein the antagonist is administered in combination with one or more vaccines, antigens, antibodies, cytotoxic agents, allergens, antibiotics, antisense oligonucleotides, TLR antagonists, peptides, proteins, gene therapy vectors, DNA vaccines, adjuvants, chemotherapeutic agents, or kinase inhibitors.

4. The method according to claim 1, wherein the route of administration is parenteral, mucosal delivery, oral, sublingual, transdermal, topical, inhalation, intranasal, aerosol, intraocular, intratracheal, intrarectal, vaginal, by gene gun, dermal patch or in eye drop or mouthwash form.

5. The method according to claim 1, wherein the mammal is a human.

6. The method according to claim 2, wherein the antagonist is administered in combination with one or more vaccines, antigens, antibodies, cytotoxic agents, allergens, antibiotics, antisense oligonucleotides, TLR antagonists, peptides, proteins, gene therapy vectors, DNA vaccines, adjuvants, chemotherapeutic agents, or kinase inhibitors.

7. The method according to claim 2, wherein the route of administration is parenteral, mucosal delivery, oral, sublingual, transdermal, topical, inhalation, intranasal, aerosol, intraocular, intratracheal, intrarectal, vaginal, by gene gun, dermal patch or in eye drop or mouthwash form.

8. The method according to claim 2, wherein the mammal is a human.

* * * * *

UNITED STATES PATENT AND TRADEMARK OFFICE
CERTIFICATE OF CORRECTION

PATENT NO. : 9,096,858 B2  
APPLICATION NO. : 13/905242  
DATED : August 4, 2015  
INVENTOR(S) : Ekambar R. Kandimalla et al.

Page 1 of 1

It is certified that error appears in the above-identified patent and that said Letters Patent is hereby corrected as shown below:

Column 70, Claim 2, line 57, delete "2-0-e-" and insert -- 2'-0-Me- --.

Signed and Sealed this  
Ninth Day of February, 2016

Michelle K. Lee  
*Director of the United States Patent and Trademark Office*

SEQUENCE LISTING

```
<160> NUMBER OF SEQ ID NOS: 72

<210> SEQ ID NO 1
<211> LENGTH: 9
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: modified_base
<222> LOCATION: (1)..(3)
<223> OTHER INFORMATION: 2'-O-Me
<220> FEATURE:
<221> NAME/KEY: modified_base
```

<222> LOCATION: (5)..(5)
<223> OTHER INFORMATION: 7-deaza-dG

<400> SEQUENCE: 1 ugucgttct                                                                                                  9

<210> SEQ ID NO 2
<211> LENGTH: 8
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: modified_base
<222> LOCATION: (1)..(3)
<223> OTHER INFORMATION: 2'-O-Me
<220> FEATURE:
<221> NAME/KEY: modified_base
<222> LOCATION: (5)..(5)
<223> OTHER INFORMATION: 7-deaza-dG

<400> SEQUENCE: 2 ugucgttc                                                                                                   8

<210> SEQ ID NO 3
<211> LENGTH: 7
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: modified_base
<222> LOCATION: (1)..(3)
<223> OTHER INFORMATION: 2'-O-Me
<220> FEATURE:
<221> NAME/KEY: modified_base
<222> LOCATION: (5)..(5)
<223> OTHER INFORMATION: 7-deaza-dG

<400> SEQUENCE: 3 ugucgtt                                                                                                    7

<210> SEQ ID NO 4
<211> LENGTH: 9
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: modified_base
<222> LOCATION: (1)..(2)
<223> OTHER INFORMATION: 2'-O-Me
<220> FEATURE:
<221> NAME/KEY: modified_base
<222> LOCATION: (4)..(4)
<223> OTHER INFORMATION: 7-deaza-dG

<400> SEQUENCE: 4 gucgttctt                                                                                                  9

<210> SEQ ID NO 5
<211> LENGTH: 9
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: modified_base
<222> LOCATION: (1)..(3)
<223> OTHER INFORMATION: 2'-O-Me
<220> FEATURE:

<221> NAME/KEY: modified_base
<222> LOCATION: (5)..(5)
<223> OTHER INFORMATION: AraG

<400> SEQUENCE: 5 ugucgttct                                                                                              9

<210> SEQ ID NO 6
<211> LENGTH: 8
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: modified_base
<222> LOCATION: (1)..(3)
<223> OTHER INFORMATION: 2'-O-Me
<220> FEATURE:
<221> NAME/KEY: modified_base
<222> LOCATION: (5)..(5)
<223> OTHER INFORMATION: AraG

<400> SEQUENCE: 6 ugucgttc                                                                                               8

<210> SEQ ID NO 7
<211> LENGTH: 9
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: modified_base
<222> LOCATION: (2)..(3)
<223> OTHER INFORMATION: 2'-O-Me
<220> FEATURE:
<221> NAME/KEY: modified_base
<222> LOCATION: (5)..(5)
<223> OTHER INFORMATION: 7-deaza-dG

<400> SEQUENCE: 7 tgucgttct                                                                                              9

<210> SEQ ID NO 8
<211> LENGTH: 11
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: modified_base
<222> LOCATION: (4)..(5)
<223> OTHER INFORMATION: 2'-O-Me
<220> FEATURE:
<221> NAME/KEY: modified_base
<222> LOCATION: (7)..(7)
<223> OTHER INFORMATION: 7-deaza-dG

<400> SEQUENCE: 8
cttgucgttc t                                                                                          11

<210> SEQ ID NO 9
<211> LENGTH: 9
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: modified_base
<222> LOCATION: (3)..(4)
<223> OTHER INFORMATION: 2'-O-Me -continued

```
<220> FEATURE:
<221> NAME/KEY: modified_base
<222> LOCATION: (6)..(6)
<223> OTHER INFORMATION: 7-deaza-dG

<400> SEQUENCE: 9 ttgucgttc                                                                  9

<210> SEQ ID NO 10
<211> LENGTH: 11
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: modified_base
<222> LOCATION: (5)..(6)
<223> OTHER INFORMATION: 2'-O-Me
<220> FEATURE:
<221> NAME/KEY: modified_base
<222> LOCATION: (8)..(8)
<223> OTHER INFORMATION: 7-deaza-dG

<400> SEQUENCE: 10
ctttgucgtt c                                                              11

<210> SEQ ID NO 11
<211> LENGTH: 9
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: modified_base
<222> LOCATION: (2)..(3)
<223> OTHER INFORMATION: 2'-O-Me
<220> FEATURE:
<221> NAME/KEY: modified_base
<222> LOCATION: (5)..(5)
<223> OTHER INFORMATION: 7-deaza-dG

<400> SEQUENCE: 11 tgucgttca                                                                  9

<210> SEQ ID NO 12
<211> LENGTH: 11
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: modified_base
<222> LOCATION: (4)..(5)
<223> OTHER INFORMATION: 2'-O-Me
<220> FEATURE:
<221> NAME/KEY: modified_base
<222> LOCATION: (7)..(7)
<223> OTHER INFORMATION: 7-deaza-dG

<400> SEQUENCE: 12
tctgacgttc t                                                              11

<210> SEQ ID NO 13
<211> LENGTH: 11
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: modified_base
<222> LOCATION: (4)..(5)
```

```
<223> OTHER INFORMATION: 2'-O-Me
<220> FEATURE:
<221> NAME/KEY: modified_base
<222> LOCATION: (7)..(7)
<223> OTHER INFORMATION: AraG

<400> SEQUENCE: 13
tctgacgttc t                                                          11

<210> SEQ ID NO 14
<211> LENGTH: 9
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: modified_base
<222> LOCATION: (3)..(4)
<223> OTHER INFORMATION: 2'-O-Me
<220> FEATURE:
<221> NAME/KEY: modified_base
<222> LOCATION: (6)..(6)
<223> OTHER INFORMATION: 7-deaza-dG

<400> SEQUENCE: 14 ttgucgtta                                                              9

<210> SEQ ID NO 15
<211> LENGTH: 11
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: modified_base
<222> LOCATION: (5)..(6)
<223> OTHER INFORMATION: 2'-O-Me
<220> FEATURE:
<221> NAME/KEY: modified_base
<222> LOCATION: (8)..(8)
<223> OTHER INFORMATION: 7-deaza-dG

<400> SEQUENCE: 15
ctctgucgtt a                                                          11

<210> SEQ ID NO 16
<211> LENGTH: 9
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: modified_base
<222> LOCATION: (4)..(4)
<223> OTHER INFORMATION: 5-Me-dC

<400> SEQUENCE: 16 tgtcgttct                                                              9

<210> SEQ ID NO 17
<211> LENGTH: 9
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: modified_base
<222> LOCATION: (4)..(4)
<223> OTHER INFORMATION: 2'-O-Me

<400> SEQUENCE: 17
``` tgtcgttct                                                                                          9

<210> SEQ ID NO 18
<211> LENGTH: 9
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: modified_base
<222> LOCATION: (5)..(5)
<223> OTHER INFORMATION: 2'-O-Me

<400> SEQUENCE: 18 tgtcgttct                                                                                          9

<210> SEQ ID NO 19
<211> LENGTH: 9
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: modified_base
<222> LOCATION: (1)..(3)
<223> OTHER INFORMATION: 2'-O-Me
<220> FEATURE:
<221> NAME/KEY: modified_base
<222> LOCATION: (5)..(5)
<223> OTHER INFORMATION: 7-deaza-dG

<400> SEQUENCE: 19 ugucgacat                                                                                          9

<210> SEQ ID NO 20
<211> LENGTH: 9
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: modified_base
<222> LOCATION: (1)..(3)
<223> OTHER INFORMATION: 2'-O-Me
<220> FEATURE:
<221> NAME/KEY: modified_base
<222> LOCATION: (5)..(5)
<223> OTHER INFORMATION: 7-deaza-dG

<400> SEQUENCE: 20 ugacgttct                                                                                          9

<210> SEQ ID NO 21
<211> LENGTH: 9
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: modified_base
<222> LOCATION: (1)..(3)
<223> OTHER INFORMATION: 2'-O-Me
<220> FEATURE:
<221> NAME/KEY: modified_base
<222> LOCATION: (4)..(4)
<223> OTHER INFORMATION: 5-Me-dC

<400> SEQUENCE: 21 ugucgttct                                                                                          9

```
<210> SEQ ID NO 22
<211> LENGTH: 9
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: modified_base
<222> LOCATION: (1)..(3)
<223> OTHER INFORMATION: 2'-O-(2-methoxyethyl)
<220> FEATURE:
<221> NAME/KEY: modified_base
<222> LOCATION: (4)..(4)
<223> OTHER INFORMATION: 5-Me-dC

<400> SEQUENCE: 22 tgtcgttct                                                                     9

<210> SEQ ID NO 23
<211> LENGTH: 9
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: modified_base
<222> LOCATION: (1)..(3)
<223> OTHER INFORMATION: 2'-O-Me
<220> FEATURE:
<221> NAME/KEY: modified_base
<222> LOCATION: (4)..(4)
<223> OTHER INFORMATION: 2'-O-Me-5-Me-C

<400> SEQUENCE: 23 ugucgttct                                                                     9

<210> SEQ ID NO 24
<211> LENGTH: 9
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: modified_base
<222> LOCATION: (1)..(3)
<223> OTHER INFORMATION: 2'-O-(2-methoxyethyl)
<220> FEATURE:
<221> NAME/KEY: modified_base
<222> LOCATION: (4)..(4)
<223> OTHER INFORMATION: 2'-O-Me-5-Me-C

<400> SEQUENCE: 24 tgtcgttct                                                                     9

<210> SEQ ID NO 25
<211> LENGTH: 9
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: modified_base
<222> LOCATION: (1)..(3)
<223> OTHER INFORMATION: 2'-O-Me
<220> FEATURE:
<221> NAME/KEY: modified_base
<222> LOCATION: (5)..(5)
<223> OTHER INFORMATION: AraG

<400> SEQUENCE: 25 ugacgttct                                                                     9
```

-continued

```
<210> SEQ ID NO 26
<211> LENGTH: 11
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: modified_base
<222> LOCATION: (4)..(5)
<223> OTHER INFORMATION: 2'-O-Me
<220> FEATURE:
<221> NAME/KEY: modified_base
<222> LOCATION: (7)..(7)
<223> OTHER INFORMATION: 7-deaza-dG

<400> SEQUENCE: 26
tctgucgttc t                                                                11

<210> SEQ ID NO 27
<211> LENGTH: 11
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: modified_base
<222> LOCATION: (4)..(5)
<223> OTHER INFORMATION: 2'-O-Me
<220> FEATURE:
<221> NAME/KEY: modified_base
<222> LOCATION: (7)..(7)
<223> OTHER INFORMATION: AraG

<400> SEQUENCE: 27
tctgucgttc t                                                                11

<210> SEQ ID NO 28
<211> LENGTH: 7
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: modified_base
<222> LOCATION: (1)..(3)
<223> OTHER INFORMATION: 2'-O-Me
<220> FEATURE:
<221> NAME/KEY: modified_base
<222> LOCATION: (5)..(5)
<223> OTHER INFORMATION: AraG

<400> SEQUENCE: 28 ugucgtt                                                                      7

<210> SEQ ID NO 29
<211> LENGTH: 9
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: modified_base
<222> LOCATION: (2)..(4)
<223> OTHER INFORMATION: 2'-O-Me
<220> FEATURE:
<221> NAME/KEY: modified_base
<222> LOCATION: (6)..(6)
<223> OTHER INFORMATION: 7-deaza-dG

<400> SEQUENCE: 29
``` tugucgttc                                                                                                    9

<210> SEQ ID NO 30
<211> LENGTH: 9
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: modified_base
<222> LOCATION: (3)..(5)
<223> OTHER INFORMATION: 2'-O-Me
<220> FEATURE:
<221> NAME/KEY: modified_base
<222> LOCATION: (7)..(7)
<223> OTHER INFORMATION: 7-deaza-dG

<400> SEQUENCE: 30 ctugucgtt                                                                                                    9

<210> SEQ ID NO 31
<211> LENGTH: 9
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: modified_base
<222> LOCATION: (1)..(1)
<223> OTHER INFORMATION: 2'-O-Me
<220> FEATURE:
<221> NAME/KEY: modified_base
<222> LOCATION: (3)..(3)
<223> OTHER INFORMATION: 7-deaza-dG

<400> SEQUENCE: 31 ucgttcttc                                                                                                    9

<210> SEQ ID NO 32
<211> LENGTH: 18
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: modified_base
<222> LOCATION: (7)..(8)
<223> OTHER INFORMATION: 2'-O-Me
<220> FEATURE:
<221> NAME/KEY: modified_base
<222> LOCATION: (9)..(9)
<223> OTHER INFORMATION: 5-Me-dC

<400> SEQUENCE: 32
ctatctgacg ttctctgt                                                                                         18

<210> SEQ ID NO 33
<211> LENGTH: 18
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: modified_base
<222> LOCATION: (7)..(9)
<223> OTHER INFORMATION: 2'-O-Me

<400> SEQUENCE: 33
ctatctgacg ttctctgt                                                                                         18

-continued

```
<210> SEQ ID NO 34
<211> LENGTH: 18
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: modified_base
<222> LOCATION: (7)..(8)
<223> OTHER INFORMATION: 2'-O-Me
<220> FEATURE:
<221> NAME/KEY: modified_base
<222> LOCATION: (9)..(9)
<223> OTHER INFORMATION: 2'-O-Me-5-Me-C

<400> SEQUENCE: 34
ctatctgacg ttctctgt                                                 18

<210> SEQ ID NO 35
<211> LENGTH: 18
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: modified_base
<222> LOCATION: (7)..(8)
<223> OTHER INFORMATION: 2'-O-Me
<220> FEATURE:
<221> NAME/KEY: modified_base
<222> LOCATION: (10)..(10)
<223> OTHER INFORMATION: 2'-O-Me

<400> SEQUENCE: 35
ctatctgacg ttctctgt                                                 18

<210> SEQ ID NO 36
<211> LENGTH: 18
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: modified_base
<222> LOCATION: (7)..(8)
<223> OTHER INFORMATION: 2'-O-(2-methoxyethyl)

<400> SEQUENCE: 36
ctatctgacg ttctctgt                                                 18

<210> SEQ ID NO 37
<211> LENGTH: 18
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: modified_base
<222> LOCATION: (7)..(8)
<223> OTHER INFORMATION: 2'-O-Me
<220> FEATURE:
<221> NAME/KEY: modified_base
<222> LOCATION: (9)..(9)
<223> OTHER INFORMATION: 5-Me-dC

<400> SEQUENCE: 37
ctatctgucg ttctctgt                                                 18

<210> SEQ ID NO 38
<211> LENGTH: 18
<212> TYPE: DNA
```

```
<213> ORGANISM: Artificial Sequence
<220> FEATURE:
<223> OTHER INFORMATION: Synthetic oligonucleotide
<220> FEATURE:
<221> NAME/KEY: modified_base
<222> LOCATION: (7)..(9)
<223> OTHER INFORMATION: 2'-O-Me

<400> SEQUENCE: 38
ctatctgucg ttctctgt                                                    18

<210> SEQ ID NO 39
<211> LENGTH: 18
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: modified_base
<222> LOCATION: (7)..(8)
<223> OTHER INFORMATION: 2'-O-Me
<220> FEATURE:
<221> NAME/KEY: modified_base
<222> LOCATION: (9)..(9)
<223> OTHER INFORMATION: 2'-O-Me-5-Me-C

<400> SEQUENCE: 39
ctatctgucg ttctctgt                                                    18

<210> SEQ ID NO 40
<211> LENGTH: 18
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: modified_base
<222> LOCATION: (7)..(8)
<223> OTHER INFORMATION: 2'-O-Me
<220> FEATURE:
<221> NAME/KEY: modified_base
<222> LOCATION: (10)..(10)
<223> OTHER INFORMATION: 2'-O-Me

<400> SEQUENCE: 40
ctatctgucg ttctctgt                                                    18

<210> SEQ ID NO 41
<211> LENGTH: 11
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: modified_base
<222> LOCATION: (4)..(5)
<223> OTHER INFORMATION: 2'-O-Me
<220> FEATURE:
<221> NAME/KEY: modified_base
<222> LOCATION: (6)..(6)
<223> OTHER INFORMATION: 5-Me-dC
<220> FEATURE:
<221> NAME/KEY: modified_base
<222> LOCATION: (7)..(7)
<223> OTHER INFORMATION: 7-deaza-dG

<400> SEQUENCE: 41
cttgucgttc t                                                           11

<210> SEQ ID NO 42
<211> LENGTH: 18
```

```
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: modified_base
<222> LOCATION: (7)..(8)
<223> OTHER INFORMATION: 2'-O-Me
<220> FEATURE:
<221> NAME/KEY: modified_base
<222> LOCATION: (9)..(9)
<223> OTHER INFORMATION: 5-Me-dC
<220> FEATURE:
<221> NAME/KEY: modified_base
<222> LOCATION: (10)..(10)
<223> OTHER INFORMATION: 7-deaza-dG
<220> FEATURE:
<221> NAME/KEY: modified_base
<222> LOCATION: (17)..(18)
<223> OTHER INFORMATION: 2'-O-Me

<400> SEQUENCE: 42
ctatctgucg ttctctgu                                                 18

<210> SEQ ID NO 43
<211> LENGTH: 9
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: modified_base
<222> LOCATION: (2)..(3)
<223> OTHER INFORMATION: 2'-O-Me
<220> FEATURE:
<221> NAME/KEY: modified_base
<222> LOCATION: (4)..(4)
<223> OTHER INFORMATION: 5-Me-dC
<220> FEATURE:
<221> NAME/KEY: modified_base
<222> LOCATION: (5)..(5)
<223> OTHER INFORMATION: 7-deaza-dG

<400> SEQUENCE: 43 tgucgttct                                                            9

<210> SEQ ID NO 44
<211> LENGTH: 11
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: modified_base
<222> LOCATION: (5)..(6)
<223> OTHER INFORMATION: 2'-O-Me
<220> FEATURE:
<221> NAME/KEY: modified_base
<222> LOCATION: (7)..(7)
<223> OTHER INFORMATION: 5-Me-dC
<220> FEATURE:
<221> NAME/KEY: modified_base
<222> LOCATION: (8)..(8)
<223> OTHER INFORMATION: 7-deaza-dG

<400> SEQUENCE: 44
ctttgucgtt c                                                        11

<210> SEQ ID NO 45
<211> LENGTH: 9
<212> TYPE: DNA
<213> ORGANISM: Artificial Sequence
<220> FEATURE:
```

```
<223> OTHER INFORMATION: Synthetic oligonucleotide
<220> FEATURE:
<221> NAME/KEY: modified_base
<222> LOCATION: (1)..(2)
<223> OTHER INFORMATION: 2'-O-Me
<220> FEATURE:
<221> NAME/KEY: modified_base
<222> LOCATION: (3)..(3)
<223> OTHER INFORMATION: 5-Me-dC
<220> FEATURE:
<221> NAME/KEY: modified_base
<222> LOCATION: (4)..(4)
<223> OTHER INFORMATION: 7-deaza-dG

<400> SEQUENCE: 45 gucgttctt                                                                    9

<210> SEQ ID NO 46
<211> LENGTH: 9
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: modified_base
<222> LOCATION: (2)..(3)
<223> OTHER INFORMATION: 2'-O-Me
<220> FEATURE:
<221> NAME/KEY: modified_base
<222> LOCATION: (4)..(4)
<223> OTHER INFORMATION: 5-Me-dC
<220> FEATURE:
<221> NAME/KEY: modified_base
<222> LOCATION: (5)..(5)
<223> OTHER INFORMATION: 7-deaza-dG

<400> SEQUENCE: 46 tgucgttca                                                                    9

<210> SEQ ID NO 47
<211> LENGTH: 11
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: modified_base
<222> LOCATION: (4)..(5)
<223> OTHER INFORMATION: 2'-O-Me
<220> FEATURE:
<221> NAME/KEY: modified_base
<222> LOCATION: (6)..(6)
<223> OTHER INFORMATION: 5-Me-dC
<220> FEATURE:
<221> NAME/KEY: modified_base
<222> LOCATION: (7)..(7)
<223> OTHER INFORMATION: AraG

<400> SEQUENCE: 47
cttgucgttc t                                                                11

<210> SEQ ID NO 48
<211> LENGTH: 10
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: modified_base
<222> LOCATION: (4)..(5)
<223> OTHER INFORMATION: 2'-O-Me
<220> FEATURE:
<221> NAME/KEY: modified_base
```

```
<222> LOCATION: (6)..(6)
<223> OTHER INFORMATION: 5-Me-dC
<220> FEATURE:
<221> NAME/KEY: modified_base
<222> LOCATION: (7)..(7)
<223> OTHER INFORMATION: 7-deaza-dG

<400> SEQUENCE: 48
cttgucgttc                                                                      10

<210> SEQ ID NO 49
<211> LENGTH: 11
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: modified_base
<222> LOCATION: (3)..(4)
<223> OTHER INFORMATION: 2'-O-Me
<220> FEATURE:
<221> NAME/KEY: modified_base
<222> LOCATION: (5)..(5)
<223> OTHER INFORMATION: 5-Me-dC
<220> FEATURE:
<221> NAME/KEY: modified_base
<222> LOCATION: (6)..(6)
<223> OTHER INFORMATION: 7-deaza-dG

<400> SEQUENCE: 49
ctgucgttct t                                                                    11

<210> SEQ ID NO 50
<211> LENGTH: 9
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: modified_base
<222> LOCATION: (1)..(3)
<223> OTHER INFORMATION: 2'-O-Me
<220> FEATURE:
<221> NAME/KEY: modified_base
<222> LOCATION: (4)..(4)
<223> OTHER INFORMATION: 5-Me-dC
<220> FEATURE:
<221> NAME/KEY: modified_base
<222> LOCATION: (5)..(5)
<223> OTHER INFORMATION: 7-deaza-dG

<400> SEQUENCE: 50 ugucgttct                                                                       9

<210> SEQ ID NO 51
<211> LENGTH: 9
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: modified_base
<222> LOCATION: (1)..(3)
<223> OTHER INFORMATION: 2'-O-Me
<220> FEATURE:
<221> NAME/KEY: modified_base
<222> LOCATION: (4)..(4)
<223> OTHER INFORMATION: 5-Me-dC
<220> FEATURE:
<221> NAME/KEY: modified_base
<222> LOCATION: (5)..(5)
<223> OTHER INFORMATION: AraG
```

```
<400> SEQUENCE: 51 ugucgttct                                                                    9

<210> SEQ ID NO 52
<211> LENGTH: 8
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: modified_base
<222> LOCATION: (1)..(3)
<223> OTHER INFORMATION: 2'-O-Me
<220> FEATURE:
<221> NAME/KEY: modified_base
<222> LOCATION: (4)..(4)
<223> OTHER INFORMATION: 5-Me-dC
<220> FEATURE:
<221> NAME/KEY: modified_base
<222> LOCATION: (5)..(5)
<223> OTHER INFORMATION: 7-deaza-dG

<400> SEQUENCE: 52 ugucgttc                                                                     8

<210> SEQ ID NO 53
<211> LENGTH: 18
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: modified_base
<222> LOCATION: (7)..(8)
<223> OTHER INFORMATION: 2'-O-Me
<220> FEATURE:
<221> NAME/KEY: modified_base
<222> LOCATION: (9)..(9)
<223> OTHER INFORMATION: 5-Me-dC
<220> FEATURE:
<221> NAME/KEY: modified_base
<222> LOCATION: (10)..(10)
<223> OTHER INFORMATION: 7-deaza-dG

<400> SEQUENCE: 53
ctatctgucg ttctctgt                                                         18

<210> SEQ ID NO 54
<211> LENGTH: 18
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: modified_base
<222> LOCATION: (8)..(8)
<223> OTHER INFORMATION: 2'-O-Me
<220> FEATURE:
<221> NAME/KEY: modified_base
<222> LOCATION: (9)..(9)
<223> OTHER INFORMATION: 5-Me-dC
<220> FEATURE:
<221> NAME/KEY: modified_base
<222> LOCATION: (10)..(10)
<223> OTHER INFORMATION: 7-deaza-dG

<400> SEQUENCE: 54
ctatctgucg ttctctgt                                                         18

<210> SEQ ID NO 55
<211> LENGTH: 9
```

```
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: modified_base
<222> LOCATION: (2)..(3)
<223> OTHER INFORMATION: 2'-O-Me
<220> FEATURE:
<221> NAME/KEY: modified_base
<222> LOCATION: (4)..(4)
<223> OTHER INFORMATION: 5-Me-dC
<220> FEATURE:
<221> NAME/KEY: modified_base
<222> LOCATION: (5)..(5)
<223> OTHER INFORMATION: 7-deaza-dG

<400> SEQUENCE: 55 tgacgttct                                                                    9

<210> SEQ ID NO 56
<211> LENGTH: 11
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: modified_base
<222> LOCATION: (4)..(5)
<223> OTHER INFORMATION: 2'-O-Me
<220> FEATURE:
<221> NAME/KEY: modified_base
<222> LOCATION: (6)..(6)
<223> OTHER INFORMATION: 5-Me-dC
<220> FEATURE:
<221> NAME/KEY: modified_base
<222> LOCATION: (7)..(7)
<223> OTHER INFORMATION: 7-deaza-dG

<400> SEQUENCE: 56
cttgacgttc t                                                                11

<210> SEQ ID NO 57
<211> LENGTH: 11
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: modified_base
<222> LOCATION: (5)..(6)
<223> OTHER INFORMATION: 2'-O-Me
<220> FEATURE:
<221> NAME/KEY: modified_base
<222> LOCATION: (7)..(7)
<223> OTHER INFORMATION: 5-Me-dC
<220> FEATURE:
<221> NAME/KEY: modified_base
<222> LOCATION: (8)..(8)
<223> OTHER INFORMATION: 7-deaza-dG

<400> SEQUENCE: 57
ctttgacgtt c                                                                11

<210> SEQ ID NO 58
<211> LENGTH: 9
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: modified_base
<222> LOCATION: (1)..(2)
```

```
<223> OTHER INFORMATION: 2'-O-Me
<220> FEATURE:
<221> NAME/KEY: modified_base
<222> LOCATION: (3)..(3)
<223> OTHER INFORMATION: 5-Me-dC
<220> FEATURE:
<221> NAME/KEY: modified_base
<222> LOCATION: (4)..(4)
<223> OTHER INFORMATION: 7-deaza-dG

<400> SEQUENCE: 58 gacgttctt                                                                  9

<210> SEQ ID NO 59
<211> LENGTH: 9
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: modified_base
<222> LOCATION: (2)..(3)
<223> OTHER INFORMATION: 2'-O-Me
<220> FEATURE:
<221> NAME/KEY: modified_base
<222> LOCATION: (4)..(4)
<223> OTHER INFORMATION: 5-Me-dC
<220> FEATURE:
<221> NAME/KEY: modified_base
<222> LOCATION: (5)..(5)
<223> OTHER INFORMATION: 7-deaza-dG

<400> SEQUENCE: 59 tgacgttca                                                                  9

<210> SEQ ID NO 60
<211> LENGTH: 11
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: modified_base
<222> LOCATION: (4)..(5)
<223> OTHER INFORMATION: 2'-O-Me
<220> FEATURE:
<221> NAME/KEY: modified_base
<222> LOCATION: (6)..(6)
<223> OTHER INFORMATION: 5-Me-dC
<220> FEATURE:
<221> NAME/KEY: modified_base
<222> LOCATION: (7)..(7)
<223> OTHER INFORMATION: AraG

<400> SEQUENCE: 60
cttgacgttc t                                                              11

<210> SEQ ID NO 61
<211> LENGTH: 10
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: modified_base
<222> LOCATION: (4)..(5)
<223> OTHER INFORMATION: 2'-O-Me
<220> FEATURE:
<221> NAME/KEY: modified_base
<222> LOCATION: (6)..(6)
<223> OTHER INFORMATION: 5-Me-dC
<220> FEATURE:
<221> NAME/KEY: modified_base
```

```
<222> LOCATION: (7)..(7)
<223> OTHER INFORMATION: 7-deaza-dG

<400> SEQUENCE: 61
cttgacgttc                                                          10

<210> SEQ ID NO 62
<211> LENGTH: 11
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: modified_base
<222> LOCATION: (3)..(4)
<223> OTHER INFORMATION: 2'-O-Me
<220> FEATURE:
<221> NAME/KEY: modified_base
<222> LOCATION: (5)..(5)
<223> OTHER INFORMATION: 5-Me-dC
<220> FEATURE:
<221> NAME/KEY: modified_base
<222> LOCATION: (6)..(6)
<223> OTHER INFORMATION: 7-deaza-dG

<400> SEQUENCE: 62
ctgacgttct t                                                        11

<210> SEQ ID NO 63
<211> LENGTH: 9
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: modified_base
<222> LOCATION: (1)..(3)
<223> OTHER INFORMATION: 2'-O-Me
<220> FEATURE:
<221> NAME/KEY: modified_base
<222> LOCATION: (4)..(4)
<223> OTHER INFORMATION: 5-Me-dC
<220> FEATURE:
<221> NAME/KEY: modified_base
<222> LOCATION: (5)..(5)
<223> OTHER INFORMATION: 7-deaza-dG

<400> SEQUENCE: 63 ugacgttct                                                           9

<210> SEQ ID NO 64
<211> LENGTH: 9
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: modified_base
<222> LOCATION: (1)..(3)
<223> OTHER INFORMATION: 2'-O-Me
<220> FEATURE:
<221> NAME/KEY: modified_base
<222> LOCATION: (4)..(4)
<223> OTHER INFORMATION: 5-Me-dC
<220> FEATURE:
<221> NAME/KEY: modified_base
<222> LOCATION: (5)..(5)
<223> OTHER INFORMATION: AraG

<400> SEQUENCE: 64 ugacgttct                                                           9
```

```
<210> SEQ ID NO 65
<211> LENGTH: 8
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: modified_base
<222> LOCATION: (1)..(3)
<223> OTHER INFORMATION: 2'-O-Me
<220> FEATURE:
<221> NAME/KEY: modified_base
<222> LOCATION: (4)..(4)
<223> OTHER INFORMATION: 5-Me-dC
<220> FEATURE:
<221> NAME/KEY: modified_base
<222> LOCATION: (5)..(5)
<223> OTHER INFORMATION: 7-deaza-dG

<400> SEQUENCE: 65 ugacgttc                                                                   8

<210> SEQ ID NO 66
<211> LENGTH: 18
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: modified_base
<222> LOCATION: (7)..(8)
<223> OTHER INFORMATION: 2'-O-Me
<220> FEATURE:
<221> NAME/KEY: modified_base
<222> LOCATION: (9)..(9)
<223> OTHER INFORMATION: 5-Me-dC
<220> FEATURE:
<221> NAME/KEY: modified_base
<222> LOCATION: (10)..(10)
<223> OTHER INFORMATION: 7-deaza-dG

<400> SEQUENCE: 66
ctatctgacg ttctctgt                                                       18

<210> SEQ ID NO 67
<211> LENGTH: 18
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: modified_base
<222> LOCATION: (8)..(8)
<223> OTHER INFORMATION: 2'-O-Me
<220> FEATURE:
<221> NAME/KEY: modified_base
<222> LOCATION: (9)..(9)
<223> OTHER INFORMATION: 5-Me-dC
<220> FEATURE:
<221> NAME/KEY: modified_base
<222> LOCATION: (10)..(10)
<223> OTHER INFORMATION: 7-deaza-dG

<400> SEQUENCE: 67
ctatctgacg ttctctgt                                                       18

<210> SEQ ID NO 68
<211> LENGTH: 18
<212> TYPE: DNA
<213> ORGANISM: Artificial Sequence
<220> FEATURE:
<223> OTHER INFORMATION: Synthetic oligonucleotide
```

```
<220> FEATURE:
<221> NAME/KEY: modified_base
<222> LOCATION: (7)..(8)
<223> OTHER INFORMATION: 2'-O-Me
<220> FEATURE:
<221> NAME/KEY: modified_base
<222> LOCATION: (9)..(9)
<223> OTHER INFORMATION: 5-Me-dC
<220> FEATURE:
<221> NAME/KEY: modified_base
<222> LOCATION: (10)..(10)
<223> OTHER INFORMATION: 7-deaza-dG
<220> FEATURE:
<221> NAME/KEY: modified_base
<222> LOCATION: (17)..(18)
<223> OTHER INFORMATION: 2'-O-Me

<400> SEQUENCE: 68
ctatctgacg ttctctgu                                                   18

<210> SEQ ID NO 69
<211> LENGTH: 9
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: modified_base
<222> LOCATION: (4)..(4)
<223> OTHER INFORMATION: 2'-O-Me-5-Me-C

<400> SEQUENCE: 69 tgtcgttct                                                              9

<210> SEQ ID NO 70
<211> LENGTH: 10
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<223> OTHER INFORMATION: m = 0-30
<220> FEATURE:
<221> NAME/KEY: misc_feature
<222> LOCATION: (1)..(4)
<223> OTHER INFORMATION: n is a, c, g, or t
<220> FEATURE:
<221> NAME/KEY: misc_feature
<222> LOCATION: (7)..(10)
<223> OTHER INFORMATION: n is a, c, g, or t

<400> SEQUENCE: 70 nnnncgnnnn                                                            10

<210> SEQ ID NO 71
<211> LENGTH: 12
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<223> OTHER INFORMATION: z/p = 0-30
<220> FEATURE:
<221> NAME/KEY: misc_feature
<222> LOCATION: (1)..(2)
<223> OTHER INFORMATION: n is a, c, g, or t
<220> FEATURE:
<221> NAME/KEY: misc_feature
<222> LOCATION: (3)..(4)
<223> OTHER INFORMATION: 2'-O-Me
<220> FEATURE:
```

```
<221> NAME/KEY: misc_feature
<222> LOCATION: (5)..(5)
<223> OTHER INFORMATION: 5-Me-dC
<220> FEATURE:
<221> NAME/KEY: misc_feature
<222> LOCATION: (6)..(6)
<223> OTHER INFORMATION: 7-deaza-dG
<220> FEATURE:
<221> NAME/KEY: misc_feature
<222> LOCATION: (7)..(10)
<223> OTHER INFORMATION: n is a, c, g, or t
<220> FEATURE:
<221> NAME/KEY: misc_feature
<222> LOCATION: (11)..(12)
<223> OTHER INFORMATION: 2'-O-Me

<400> SEQUENCE: 71
nnnncgnnnn nn                                                      12

<210> SEQ ID NO 72
<211> LENGTH: 18
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (1)..(6)
<223> OTHER INFORMATION: n is a, c, g, or t
<220> FEATURE:
<221> NAME/KEY: misc_feature
<222> LOCATION: (7)..(8)
<223> OTHER INFORMATION: 2'-O-Me
<220> FEATURE:
<221> NAME/KEY: misc_feature
<222> LOCATION: (9)..(9)
<223> OTHER INFORMATION: 5-Me-dC
<220> FEATURE:
<221> NAME/KEY: misc_feature
<222> LOCATION: (10)..(10)
<223> OTHER INFORMATION: 7-deaza-dG
<220> FEATURE:
<221> NAME/KEY: misc_feature
<222> LOCATION: (11)..(16)
<223> OTHER INFORMATION: n is a, c, g, or t
<220> FEATURE:
<221> NAME/KEY: misc_feature
<222> LOCATION: (17)..(18)
<223> OTHER INFORMATION: 2'-O-Me

<400> SEQUENCE: 72
nnnnnnnncg nnnnnnnn                                                18
```